United States Patent
Astrom et al.

(10) Patent No.: US 9,713,722 B1
(45) Date of Patent: Jul. 25, 2017

(54) ALTERNATIVE ELECTRODE CONFIGURATIONS FOR REDUCED POWER CONSUMPTION

(71) Applicant: Medtronic Bakken Research Center B.V., Maastricht (NL)

(72) Inventors: Mattias Bengt Johan Astrom, Vasteras (NL); Jeroen Jacob Arnold Tol, Eindhoven (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 0 days.

(21) Appl. No.: 15/143,245

(22) Filed: Apr. 29, 2016

(51) Int. Cl.
*A61N 1/36* (2006.01)
*A61N 1/05* (2006.01)
*A61N 1/372* (2006.01)

(52) U.S. Cl.
CPC ....... *A61N 1/36185* (2013.01); *A61N 1/0534* (2013.01); *A61N 1/37247* (2013.01)

(58) Field of Classification Search
CPC A61N 1/36185; A61N 1/0529–1/0534; A61N 1/0553; A61N 1/08; A61N 2001/083
See application file for complete search history.

(56) References Cited

U.S. PATENT DOCUMENTS

| | | | |
|---|---|---|---|
| 8,024,049 B1 | 9/2011 | Gilson et al. | |
| 9,031,658 B2 | 5/2015 | Chiao et al. | |
| 9,084,900 B2 | 7/2015 | Hershey et al. | |
| 9,186,510 B2 | 11/2015 | Gliner et al. | |
| 2006/0184209 A1 | 8/2006 | John et al. | |
| 2008/0058893 A1 | 3/2008 | Naujokat et al. | |
| 2010/0168603 A1 | 7/2010 | Himes et al. | |
| 2011/0184487 A1 | 7/2011 | Alberts et al. | |
| 2014/0243925 A1 | 8/2014 | Kothandaraman | |
| 2014/0350635 A1 | 11/2014 | Strother et al. | |

(Continued)

FOREIGN PATENT DOCUMENTS

WO 2011107917 A1 9/2011

OTHER PUBLICATIONS

Ghovanloo, et al., "A compact large Voltage-compliance high output-impedance progammable current source for implantable microstimulators," IEEE Transactions on Biomedical Engineering; vol. 52; Issue 1, Jan. 2005, pp. 97-105.

*Primary Examiner* — Michael Kahelin
(74) *Attorney, Agent, or Firm* — Shumaker & Sieffert, P.A.

(57) ABSTRACT

The disclosure describes devices and systems for determining alternative electrode combinations and power consumption for these alternative electrode combinations. In one example, a method includes identifying a set of one or more electrodes configured to deliver electrical stimulation therapy via a lead, determining, based on the set of one or more electrodes, one or more alternative electrode combinations for delivering electrical stimulation therapy, calculating, for each of the one or more alternative electrode combinations, a respective field similarity score with respect to the set of one or more electrodes, and outputting a representation of at least one of the one or more alternative electrode combinations for selection in at least partially defining electrical stimulation therapy, the representation comprising an indication of at least one of the respective power consumption values or the respective field similarity scores.

24 Claims, 12 Drawing Sheets

(56) References Cited

U.S. PATENT DOCUMENTS

2015/0174408 A1   6/2015   Grill et al.
2015/0258339 A1   9/2015   Burchiel et al.
2016/0030749 A1*  2/2016   Carcieri ............ A61N 1/36128
                                                                607/45

* cited by examiner

ALTERNATIVE ELECTRODE CONFIGURATIONS FOR REDUCED POWER CONSUMPTION

TECHNICAL FIELD

The disclosure relates to electrical stimulation and, more particularly, selection of stimulation parameters for electrical stimulation therapy.

BACKGROUND

Implantable neurostimulation devices have been used to treat acute or chronic neurological conditions. Deep brain stimulation (DBS), the mild electrical stimulation of subcortical structures, belongs to this category of implantable devices, and has been shown to be therapeutically effective for Parkinson's disease, Dystonia, Essential Tremor, Obsessive Compulsive Disorder, and Epilepsy. New applications of DBS in the domain of psychiatric disorders (clinical depression, anorexia nervosa, schizophrenia) are being researched. In some example systems, a lead carrying four ring electrodes at its distal portion is connected to an implantable pulse generator to deliver electrical stimulation therapy.

SUMMARY

In general, the disclosure describes techniques, devices, and systems for determining alternative electrode combinations that may provide reduced power consumption during stimulation therapy while maintaining appropriate stimulation fields. A user or system may identify a set of one or more electrodes as a starting point or constraint for generation of different alternative electrode combinations. The identified set of one or more electrodes may correspond to selected electrodes from a user, electrodes associated with a user selected set of stimulation parameters or system selected set of stimulation parameters, or even one or more electrodes that correspond to an initial volume of tissue targeted for activation by electrical stimulation. In one example, the system may receive an initial electrode combination (e.g., a set of one or more electrodes from user input or from a selected set of stimulation parameters) that provides a desired or intended stimulation field (e.g., a volume of neural activation, a volume of tissue activation, or an electric potential distribution) to stimulate a specific anatomical region. The system may identify alternative electrode combinations that may provide stimulation therapy that consumes less power than the set of one or more electrodes, or the initial electrode combination, but deliver a stimulation field similar to the stimulation field deliverable with the set of one or more electrodes.

For example, the system may determine alternative electrode combinations that are associated with a lower collective impedance than the collective impedance associated with the set of one or more electrodes originally identified. The lower collective impedance may be due to the alternative electrode combinations having additional electrodes over an initial electrode combination in order to reduce the impedance of the electrodes and thus reduce the total power necessary to deliver stimulation at the same current level. In other examples, one or more alternative electrode combinations may include the same or fewer electrodes than the initial electrode combination but include lower resistance tissue across which stimulation current travels. The system may display, for an electrode combination selection by a user, a representation of the power consumption values and/or the similarity of the stimulation fields generated by the one or more alternative electrode combinations with respect to the stimulation field associated with the set of one or more electrodes (e.g., the initial electrode combination) for one or more alternative electrode combination. In other examples, the system may automatically select an alternative electrode combination according to the reduced power consumption values and/or similarity of the stimulation field.

In one example, the disclosure is directed to a method that includes identifying, by one or more processors, a set of one or more electrodes configured to deliver electrical stimulation therapy via a lead, the lead comprising a plurality of electrodes arranged in a complex electrode array geometry, wherein the plurality of electrodes comprises the set of one or more electrodes, determining, by the one or more processors and based on the set of one or more electrodes, one or more alternative electrode combinations for delivering electrical stimulation therapy, wherein each of the one or more alternative electrode combinations are associated with a respective power consumption value lower than a power consumption value associated with the set of one or more electrodes, calculating, by the one or more processors and for each of the one or more alternative electrode combinations, a respective field similarity score with respect to the set of one or more electrodes, and outputting, by the one or more processors, a representation of at least one of the one or more alternative electrode combinations for selection in at least partially defining electrical stimulation therapy, the representation comprising an indication of at least one of the respective power consumption values or the respective field similarity scores.

In another example, the disclosure is directed to a system that includes one or more processors configured to identify a set of one or more electrodes configured to deliver electrical stimulation therapy via a lead, the lead comprising a plurality of electrodes arranged in a complex electrode array geometry, wherein the plurality of electrodes comprises the set of one or more electrodes, determine, based on the set of one or more electrodes, one or more alternative electrode combinations for delivering electrical stimulation therapy, wherein each of the one or more alternative electrode combinations are associated with a respective power consumption value lower than a power consumption value associated with the set of one or more electrodes, calculate, for each of the one or more alternative electrode combinations, a respective field similarity score with respect to the set of one or more electrodes, and output a representation of at least one of the one or more alternative electrode combinations for selection in at least partially defining electrical stimulation therapy, the representation comprising an indication of at least one of the respective power consumption values or the respective field similarity scores.

In another example, the disclosure is directed to a non-transitory computer-readable medium that includes instructions that, when executed, cause one or more processors to identify a set of one or more electrodes configured to deliver electrical stimulation therapy via a lead, the lead comprising a plurality of electrodes arranged in a complex electrode array geometry, wherein the plurality of electrodes comprises the set of one or more electrodes, determine, based on the set of one or more electrodes, one or more alternative electrode combinations for delivering electrical stimulation therapy, wherein each of the one or more alternative electrode combinations are associated with a respective power consumption value lower than a power consumption value associated with the set of one or more electrodes, calculate, for each of the one or more alternative electrode combinations, a respective field similarity score with respect to the set of one or more electrodes, and output a representation of at least one of the one or more alternative electrode combinations for selection in at least partially defining electrical stimulation therapy, the representation comprising an indication of at least one of the respective power consumption values or the respective field similarity scores.

The details of one or more examples are set forth in the accompanying drawings and the description below. Other features, objects, and advantages of the disclosure will be apparent from the description and drawings, and from the claims.

DETAILED DESCRIPTION

Figure 1:
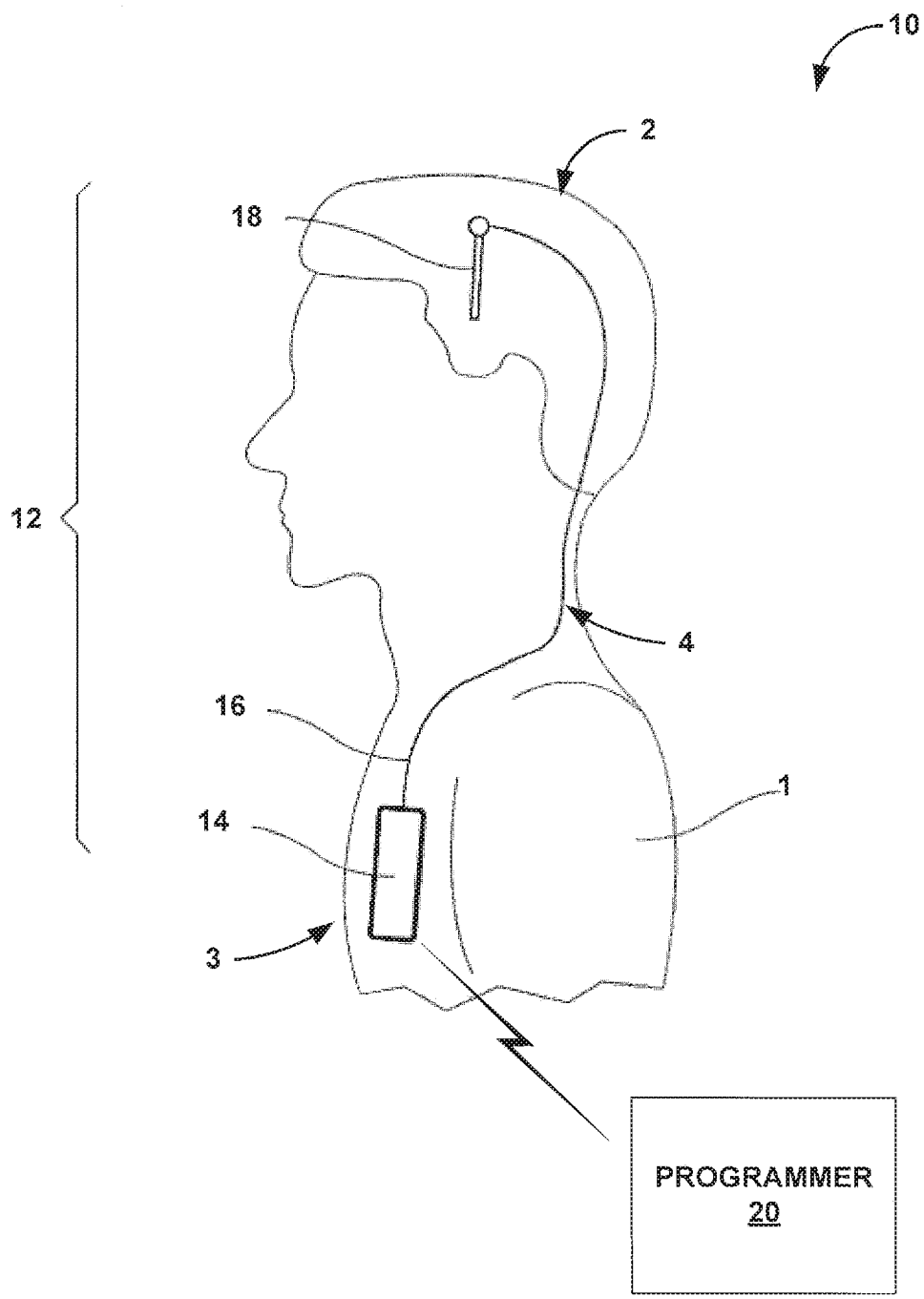
FIG. 1 a conceptual drawing of an example neurostimulation system that delivers deep brain stimulation (DBS) according to the present disclosure.

As generally described herein, systems, devices, and methods may determine alternative electrode combinations from a set of one or more electrodes (e.g., an original electrode combination) to reduce power consumption of stimulation therapy delivery while maintaining similar stimulation fields. For most electrical stimulation therapies, certain electrodes are selected in order to produce a stimulation field that affects desired nerves or neurons. In the example of deep brain stimulation (DBS), one or more leads carrying a plurality of electrodes are implanted within the deep regions of the brain. A lead may include a complex electrode array geometry, which may include electrodes at different axial positions of the lead and electrodes at different circumferential locations around the circumference of the lead (if the lead is cylindrical in shape).

The clinical benefit of DBS may be dependent upon the spatial distribution of the electric field in relation to one or more areas of the brain. Appropriate selection of electrodes may produce a stimulation field that targets certain areas to maximize therapeutic benefits while avoiding unwanted side effects that could occur if the stimulation field affects other areas of the brain. In this manner, one or more electrodes on one side of the lead may be active while other electrodes on the other side of the lead may remain unused when delivering the stimulation signal. Although fewer active electrodes may provide a more targeted stimulation field, fewer active electrodes and/or electrodes with higher surface resistivity at the tissue interface may also result in higher system impedance for delivery stimulation therapy. Other system variables, such as certain electrical components (e.g., blocking capacitors, cable resistances, current sources) in the circuitry, may also contribute to certain higher or lower impedances. This is because the power consumption P (e.g., watts) for the system (e.g., a stimulation generator) is determined by the amount of current I (e.g., total stimulation current, in amperes), its duration (e.g., stimulation pulse width, in seconds) and frequency (e.g., stimulation pulse frequency, in Hz) that is driven through the collective load or system impedance Z (e.g., connected to the stimulation generator, in ohms). In other examples, the collective load or system impedance may be represented by only its resistance, $Re(Z)$. The impedance used in determining the power consumption may be the total impedance for the entire system (e.g., a collective impedance for a circuit that includes a specified electrode combination through which the electrical stimulation pulses are delivered), such as impedances corresponding to various electrical components, electrode-tissue interfaces, and the tissue as discussed in the example of FIG. 11 and FIG. 12. The impedance may be measured or may be calculated from an electrical model of both the system and electrodes. For a system using a constant current of electrical stimulation, fewer electrodes being used in the electrode combination may generally increase the impedance, and the power consumption, of the system. Therefore, delivering electrical stimulation via fewer active electrodes can reduce the battery longevity of the implantable medical device (IMD) driving the system. As discussed above, electrodes with higher surface resistivity due to the tissue interface may also increase the effective impedance for certain electrode more than other electrodes. An increase in power consumption can decrease the duration between recharging sessions, decrease total battery longevity of the IMD, and potentially increase the frequency of surgeries required to replace IMDs at the end of battery life.

As described herein, a system identifies a set of one or more electrodes configured to deliver electrical stimulation therapy via a lead. This identification may include identifying a user defined electrode or electrode combination for stimulation, identifying one or more electrodes that can deliver a stimulation field desired (e.g., defined) by a user or selected by the system, or identifying one or more electrodes included in a set of stimulation parameters otherwise selected for defining stimulation therapy. A set of stimulation parameters, as discussed herein, may define values for electrode combinations, current or voltage amplitudes, pulse frequencies, pulse widths, duty cycle, etc. In this manner, some stimulation parameters may define the pulses that are applied to tissue via the electrode combination also defined by the set of stimulation parameters. In some examples, a stimulation program may also define the set of stimulation parameters (e.g., signal characteristics and the electrode combination through which the signal is delivered to tissue).

The system may use the identified set of one or more electrodes as a starting point, or as a constraint, on the alternative electrode combinations available for consideration. In one example generally described herein, the identified set of one or more electrodes may be an initial or original electrode combination that the alternative electrode combinations are based on. However, in the examples described herein, the set of one or more electrodes may be used as a basis for determining alternative electrode combinations instead of an initial electrode combination that the alternative electrode combinations are based on.

The system may also determine one or more alternative electrode configurations that may reduce power consumption when compared to the set of one or more electrodes, such as an initial electrode combination, while providing a similar stimulation field to the stimulation field of the initial electrode combination. The initial electrode combination may be selected by a user or otherwise identified (e.g., from a selected stimulation program, as a starting point for the general direction of stimulation from the lead, or as corresponding to a stimulation field desired by a patient) for delivery of electrical stimulation therapy. The initial electrode combination may include one or more electrodes and may be configured to operate in unipolar or bipolar configurations. The initial electrode combination may include as few as one or two electrodes that are intended to focus, or steer, the stimulation field to a desired anatomical region of the brain. However, as discussed above, few electrodes may increase the power consumption of the system when delivering stimulation therapy.

The system may determine one or more alternative electrode combinations that may provide stimulation therapy that consumes less power than the initial electrode combination but deliver a stimulation field similar to the stimulation field deliverable with the initial electrode combination. In this manner, the alternative electrode combinations may have respective collective impedances (i.e., a total impedance for a stimulation signal delivered via the alternative electrode combination) that are lower than the collective impedance of the initial electrode combination. For example, the system may add electrodes in closest proximity to the initial electrode combination to generate one alternative electrode combination. The system may continue to add the next closest electrodes to iteratively determine additional alternative electrode combinations. The greater number of electrodes in the alternative electrode combinations may generally decrease the impedance and power consumption of the system, but the corresponding stimulation field may also be increasingly dissimilar to the stimulation field of the initial electrode combination. In some examples, an alternative electrode combination may have the same or fewer electrodes of the initial electrode combination, but the electrodes of the alternative electrode combination may be associated with lower tissue impedances than the electrodes of the initial electrode combination.

The system may calculate a power consumption value and a field similarity score for each of the alternative electrode combinations. These calculations may provide objective indications of the performance of each electrode combination based on modeling of the electrode combinations. This modeling of the electrode combinations may include resistance or impedance modeling of the electrodes (e.g., an R-matrix or Z-matrix, respectively) and/or electrical field modeling and/or electrical potential distribution modeling, one, two, or all of which may be used to determine the electrical field, electrical potential distribution, volume of neuron activation (VNA), or volume of tissue activation (VTA). Axon models of brain tissue, for example, may be used to determine the VNA and VTA. In some examples, the system may present a representation of these objective measures, such as the power consumption values relative to the initial electrode combination, a numerical score indicating the similarity between stimulation fields of each alternative electrode combination and the initial electrode combination, and/or a visual representation of the stimulation fields for each alternative electrode combination. The system may be configured to receive a user input selecting one of the alternative electrode combinations for therapy. In other examples, the system may automatically select an alternative electrode combination. For example, the system may detect a loss of one or more electrodes (e.g., an electrode failure, switch failure, or conductor failure that results in the inability to deliver stimulation via an electrode) and initiate a process for selecting another electrode combination that includes available electrodes that provides similar power consumption and/or field similarity scores to the previous electrode combination that includes the now unavailable electrode(s). This process may include re-calculating the resistance and/or the impedance matrix of the remaining electrodes. In some examples, the system may store previously selected rankings of alternative electrode combinations which do not include the unavailable electrodes and automatically select a new electrode combination based on the previous ranking. The system may use the selected alternative electrode combination with or without user confirmation. In this manner, the system may use alternative electrode combinations that can reduce the power consumed during stimulation therapy while maintaining a similar stimulation field to that desired by a user.

Stimulation fields described herein may refer to different types of fields, areas, or volumes associated with the delivery of electrical stimulation. In one example, a stimulation field may refer to a volume of anatomy in which neural brain activity (in the example of deep brain stimulation) is modulated by the distribution of the stimulation pulses delivered from one or more electrodes of a stimulation lead. These types of stimulation fields may, in some examples, be referred to as a volume of neural activation (VNA) or volume of tissue activation (VTA). The VNA or VTA may be derived from simulations of the delivered electric potential distribution from the lead together with computational axon models of various sizes and/or orientations. In another example, a stimulation field may refer to the electric potential distribution or electrical gradients thereof (e.g., an electric field and/or divergence of the electric potential). In this manner, the stimulation fields described herein may provide information in the context of electrostatics and/or stimulation therapy. Any of these or other types of stimulation fields may be used to compare and/or select one or more alternative electrode combinations as described herein. In addition, each different type of stimulation field may be represented numerically or graphically.

Electrical stimulation therapy is generally described as being delivered to the patient in the absence of other therapies. However, the patient may receive electrical stimulation therapy in addition to other types of therapies such as drug delivery therapies (e.g., from the same or separate implantable device), oral medications, physical therapies, or other therapies that may address the same, related, or different conditions of the patient. The electrical stimulation therapy may be selected to work in concert with any of these therapies.

FIG. 1 a conceptual drawing of an example neurostimulation system 10 that delivers deep brain stimulation (DBS)

according to the present disclosure. In other examples, neurostimulation system 10 may be directed to other applications such as spinal cord stimulation or pelvic floor stimulation. Neurostimulation system 10 includes at least a controller 14 (e.g., an implantable medical device (IMD) and/or a first module comprising one or more pulse generators) that may be surgically implanted in the chest region 3 of a patient 1, typically below the clavicle or in the abdominal region of patient 1. Controller 14 can be configured to supply the necessary stimulation pulses, e.g., in the form of current or voltage pulses (e.g., also referred to as a stimulation signal) to lead arrangement 18. DBS system 100 may further include a connecting cable 16 (e.g., an extension wire) connected to the controller 14 and running subcutaneously to the skull 2, such as along the neck 4, where it terminates at a connector for lead arrangement 18.

DBS lead arrangement 18 may be implanted in the brain tissue, e.g., through a burr-hole in the skull. In some examples (e.g., as shown in FIGS. 2C and 3), DBS lead arrangement 18 may include one or more leads coupled to at least one module including a switch matrix. In this manner, the switch matrix may be included in a second module 111 that is separate from controller 14. In addition, DBS system 100 may include one or more grounding electrodes. The grounding electrodes may be carried by connecting cable 16, for example, between controller 14 and lead arrangement 18. In some examples, connecting cable 16 may be formed by two or more cables configured to connect to each other in parallel, and one or more of these cables may carry a grounding electrode.

Lead arrangement 18 may include a plurality of electrodes arranged in a complex electrode array geometry. A complex electrode array geometry generally refers to an arrangement of stimulation electrodes at multiple non-planar or non-coaxial positions, in contrast to simple electrode array geometries in which the electrodes share a common plane or a common axis. An example of a simple electrode array geometry is an array of ring electrodes distributed at different axial positions along the length of a cylindrical lead. Another example of a simple electrode array geometry is a planar array of electrodes on a paddle lead.

An example of a complex electrode array geometry, in accordance with this disclosure, is an array of electrodes positioned at different axial positions along the length of a lead, as well as at different angular positions about the periphery, e.g., circumference, of the lead. In some examples, electrodes in the complex electrode array geometry may include two or more electrodes (e.g., two, three, four, or more electrodes) at one axial position along the lead. This may be referred to as a "level" of the lead. The lead may also include two or more levels, whereas each level includes multiple electrodes at different angular positions. In some examples (e.g., electrodes 28 shown in the example of FIG. 2A), electrodes at one level may be staggered circumferentially with electrodes of an adjacent level. In other examples (e.g., electrodes of lead 60 in FIG. 4), electrodes at one level may be aligned circumferentially with electrodes of an adjacent level.

In some examples, the electrodes in the complex electrode array may be circular, rectangular, or non-rectangular areas of conductive material deposited at respective locations. In other examples, the electrodes in the complex electrode array geometry may appear similar to non-contiguous, arc-like segments of a conventional ring electrode. A lead with a complex electrode array geometry may include multiple "rings" of such electrode segments. Each ring is disposed at a different axial position. Each electrode segment within a given ring is disposed at a different angular position. The lead may be cylindrical or have a circular cross-section of varying diameter. Another example of a complex electrode array geometry is an array of electrodes positioned on multiple planes or faces of a non-circular lead. As an illustration, arrays of electrodes may be positioned on opposite planes of a paddle lead or multiple faces of a lead having a polygonal cross-section.

External programmer 20 wirelessly communicates with controller 14 as needed to provide or retrieve therapy information. Programmer 20 is an external computing device that the user, e.g., a clinician and/or patient 1, may use to communicate with controller 14. Programmer 20 may determine alternative electrode configurations and/or receive user selection of an alternative electrode configuration in order to reduce power consumption of the stimulation therapy, as described herein. In one example, programmer 20 may be a clinician programmer that the clinician uses to communicate with controller 14 and program one or more therapy programs for controller 14. Alternatively, programmer 20 may be a patient programmer that allows patient 1 to select programs and/or view and modify therapy parameters. The clinician programmer may include more programming features than the patient programmer. In other words, more complex or sensitive tasks may only be allowed by the clinician programmer to prevent an untrained patient from making undesirable changes to controller 14.

When programmer 20 is configured for use by the clinician, programmer 20 may be used to transmit initial programming information to controller 14. This initial information may include hardware information, such as the type of leads and the electrode arrangement, the position of leads within the brain of patient 1, the configuration of an electrode array (e.g., electrodes 132 of FIG. 2A), initial programs defining therapy parameter values such as selected electrode configurations, and any other information the clinician desires to program into controller 14.

The clinician may also store therapy programs within controller 14 with the aid of programmer 20. During a programming session, the clinician may determine one or more therapy programs that may provide efficacious therapy to patient 1 to address symptoms associated with the patient condition. For example, the clinician may select one or more stimulation electrode combinations with which stimulation is delivered to the brain. In some examples, programmer 20 may determine and present alternative electrode configurations that may consume less power during therapy and/or receive user input selecting one of the alternative electrode configurations. During the programming session, patient 1 may provide feedback to the clinician as to the efficacy of the specific program being evaluated or the clinician may evaluate the efficacy based on one or more physiological parameters of patient 1 (e.g., muscle activity or muscle tone). Programmer 20 may assist the clinician in the creation/identification of therapy programs by providing a methodical system for identifying potentially beneficial therapy parameter values.

Programmer 20 may also be configured for use by patient 1. When configured as a patient programmer, programmer 20 may have limited functionality (compared to a clinician programmer) in order to prevent patient 1 from altering critical functions of controller 14 or applications that may be detrimental to patient 1. In this manner, programmer 20 may only allow patient 1 to adjust values for certain therapy parameters or set an available range of values for a particular therapy parameter.

Neurostimulation system 10 may be implemented to provide chronic stimulation therapy to patient 1 over the course of several months or years. However, system 10 may also be employed on a trial basis to evaluate therapy before committing to full implantation. If implemented temporarily, some components of system 10 may not be implanted within patient 1. For example, patient 1 may be fitted with an external medical device, such as a trial stimulator, rather than controller 14. The external medical device may be coupled to percutaneous leads or to implanted leads via a percutaneous extension. If the trial stimulator indicates DBS system 10 provides effective treatment to patient 1, the clinician may implant a chronic stimulator within patient 1 for relatively long-term treatment. In addition, or alternative, to delivering stimulation therapy, system 10 may record neurological activity using one or more of the electrodes carried by lead assembly 18.

As described herein, system 10 may perform one or more processes in order to use an alternative electrode combination that may reduce power consumption of electrical stimulation therapy. Programmer 20 may perform this process in some examples, controller 14 may perform this process in other examples, or a combination of programmer 20 and controller 14 may perform these processes in other examples in a form of distributed computing. Alternatively, one or more networked servers may be employed to perform one or more steps of the processes described herein.

In one example, programmer 20 may, using one or more processors, receive an indication of a first electrode combination for delivering electrical stimulation therapy via a lead (e.g., lead assembly 18) that includes a complex electrode array geometry. The first electrode combination may be an initial electrode combination that defines one or more electrodes of the complex electrode array geometry as being active for delivering stimulation therapy. In some examples, a user (e.g., patient 1 or a clinician) may define the initial electrode combination in order to target a desired anatomical region of the brain. In other examples, programmer 20 may select or identify the initial electrode combination based on a user-selected program, desired anatomical region to receive stimulation therapy, or a condition to be treated. In this manner, the initial electrode combination may be a set of one or more electrodes that correspond to a VNA or VTA that covers and/or fills the desired anatomical region or area with respect to the lead to receive stimulation therapy.

Programmer 20 may then determine, based on the first electrode combination, one or more alternative electrode combinations for delivering electrical stimulation therapy. Each of the one or more alternative electrode combinations may include a greater number of electrodes than the first electrode combination. In some examples, all of the alternative electrode combinations include the electrode(s) of the first electrode combination, but in other examples the first electrode combination may not always be included in each alternative electrode combination.

For each of the one or more alternative electrode combinations, programmer 20 may calculate or measure respective power consumption values and respective field similarity scores with respect to a set of one or more electrodes, which may be a first electrode combination as described herein in some examples. In this manner, programmer 20 may compare the alternative electrode combinations to one or more aspects of the set of one or more electrodes. Programmer 20 may then generate and output a representation of at least one of the one or more alternative electrode combinations for selection in at least partially defining electrical stimulation therapy. The electrode combinations may be described as "partially defining" electrical stimulation therapy because additional stimulation parameters, such as current or voltage amplitude, pulse width, pulse frequency, etc., may also contribute to defining the electrical stimulation received by the patient. The representation may include an indication of at least one of the respective power consumption values and the respective field similarity scores for the at least one alternative electrode combination. This representation may be used to indicate what alternative electrode combination was automatically selected or to present information that the user can review prior to selecting the desired alternative electrode combination.

In some examples, programmer 20 may determine the one or more alternative electrode combinations by iteratively determining each of the one or more alternative electrode combinations such that successive alternative electrode combinations add one or more electrodes to all electrodes defined by prior alternative electrode combinations. In other words, programmer 20 may determine the alternative electrode combinations via generating different generations of electrode combinations. For example, programmer 20 may start with the initial electrode combination and then add one or more closest available electrodes to for an alternative electrode combination. The closest available electrodes may include all of the electrodes at the same distance, or equidistant, from the one or more electrodes of the initial electrode combination. Additional alternative electrode combinations may continue to be determined by adding the next closest available electrodes. Thus, successive alternative electrode combinations, or further generations, include electrodes at increasing distances from one or more electrodes of the first electrode combination. In other examples, programmer 20 may perform an exhaustive search for alternative electrode combinations that satisfy constraints that may be based on the initial electrode combination. In some cases, one or more alternative electrode combinations may have fewer electrodes than the initial electrode combination, but the fewer electrodes may be associated with lower impedances that may be due to adjacent tissue having lower resistance than the tissue surrounding electrodes of the initial electrode combination. In this manner, a first alternative electrode combination of the one or more alternative electrode combinations may include a first number of electrodes less than or equal to a second number of electrodes of the initial electrode combination, and a first power consumption value associated with the first alternative electrode combination is less than a second power consumption value associated with the initial electrode combination.

Programmer 20 may also generate information that allows each alternative electrode combination to be compared to the initial electrode combination. This information may be based on power consumption values and stimulation fields for each electrode combination. For example, programmer 20 may calculate respective power consumption values by calculating, for each of the set of one or more electrodes (e.g., a first electrode combination) and the one or more alternative electrode combinations, the power dissipated in a respective system impedance associated with the respective electrode combination (i.e., a system impedance or collective impedance) for a set of common stimulation parameters (e.g., stimulation amplitudes, pulse widths, pulse frequencies etc.). The power dissipation may be determined using an R-matrix, Z-matrix, and/or an electrical model of system 10 that is used to deliver electrical stimulation using a common set of stimulation parameters (for different electrode combinations in some examples), different sets of stimulation parameters (for the same electrode combinations in some examples), or different sets of stimulation parameters for different electrode combinations. For example, the common current value may be a stimulation current of 1.5 milliamps (mA), although lower or higher current values may be used. The common current value may be selected based on currents intended for use on the particular patient. In some examples, different currents, pulse widths, pulse frequencies etc. may be used for different electrode combinations. The power consumption value described herein may refer to an average power consumption value that takes into account pulse delivery times, non-pulse delivery times, and pulse frequency. Therefore, the power consumption value may take into account the pulse width, or duty cycle, and the frequency of the delivered pulses and generate the power consumption value to reflect the power used over any given cycle of stimulation delivery. In other examples, an "energy consumption value" per unit of time may be used to reflect this average power consumption. In any case, programmer 20 may thus use the stimulation parameters to calculate the respective power consumption value for each electrode combination (e.g., for comparison purposes). The collective impedance of each electrode combination may be calculated based on known or measured impedances of system electrical components, electrode-tissue interfaces, and tissue resistance (e.g., from a known or measured R-matrix or Z-matrix). Example contributing elements are described in FIG. 11 and FIG. 12. In other examples, power monitor 109 of FIG. 5, for example, may be used to measure actual power consumption of one or more electrode combinations.

In some examples, the resistance, or impedance, of each electrode in the complex electrode array geometry of the lead (e.g., lead assembly 18) may change over time. Electrodes may become encapsulated in tissues of various densities and/or shift slightly over time. Therefore, the tissue/ electrode interface may be altered over time and the effective impedance of tissue, and each electrode used in an electrode combination, may change. Controller 14 may periodically, or upon command, measure the impedance of each electrode of the lead or the complete resistance or impedance matrix (e.g., R-matrix or Z-matrix) of the lead. Programmer 20 may thus use the most recent measured impedance values for the electrodes when calculating the overall impedance of the initial and/or alternative electrode combinations. In some examples, programmer 20 may periodically, upon command, or in response to detected increases in power consumption, re-calculate alternative electrode combinations during the life of system 10 in order to maintain efficiency energy usage by system 10.

When presenting the alternative electrode combinations to a user, programmer 20 may rank the alternative electrode combinations based on the respective power consumption value such that the representation of at least some of the one or more alternative electrode combinations is indicative of the ranking. For example, programmer 20 may rank the alternative electrode combinations according to reduced energy consumption. The ranking may include the initial electrode combination as well. The power consumption values may be an absolute amount of energy used per unit time, a percentage of energy used when compared to the initial electrode combination, or a percentage of energy savings as compared to the initial electrode combination. In one example, the power consumption may be calculated using resistances or impedances determined using the R-matrix or Z-matrix approach, as discussed further below in relation to FIG. 12. In some examples, the power consumption values may be represented by the amount of time the battery of controller 14 will last before recharging when using the respective electrode combination.

Programmer 20 may also calculate a field similarity score for each of the alternative electrode combinations as a comparison to the stimulation field of the initial electrode combination. For example, programmer 20 may determine an original stimulation field deliverable by the initial electrode combination and determine, for each of the alternative electrode combinations, a respective stimulation field deliverable by the respective alternative electrode combination. Programmer 20 may then compare, for each of the alternative electrode combinations, the respective stimulation field deliverable by the respective alternative electrode combination to the original stimulation field deliverable by the first electrode combination. Programmer 20 may then output, for each of the alternative electrode combinations, an indication of the comparison In some examples, the field similarity score may be a numerical representation of how similar the stimulation field of the initial electrode combination is to the stimulation field of an alternative electrode combination. Programmer 20 may compare the volumes of each stimulation field and represent the field similarity score as the ratio of the two volumes. As another example, a field similarity score may indicate a percentage of the volume of the original stimulation field that overlaps with, or would share a same volume in space as, a respective stimulation field of an alternative electrode combination. Alternatively, a score may indicate a percentage of the volume of a stimulation field of an alternative electrode combination that overlaps with, or would share a same volume in space as, the original stimulation field. The field similarity score may be derived based on how two 3-D stimulation field volumes in space compare to one another (e.g., how they overlap). Alternatively, a field similarity score may indicate how one or more 2D representations of a first stimulation field compare to corresponding 2D representations of another stimulation field. Other comparison mechanisms may also be used to derive a field similarity score.

In another example, programmer 20 may calculate the field similarity score based on a Sorensen-Dice coefficient between the original stimulation field and the respective stimulation fields deliverable by the respective alternative electrode combinations. The Sorensen-Dice coefficient may be used to assess the similarity between two samples (e.g., stimulation fields) and may be calculated according to:

$$QS = \frac{2|A \cap B|}{|A| + |B|} \qquad (1)$$

where QS is the quotient of similarity with range [0, 1] with 1 being an identical match; A and B are the number of species in samples A and B. In one example, A and B may be the volume elements of the stimulation field of the initial electrode combination and the stimulation field of the respective alternative electrode combination. Any other metric that describes how one field is similar to (e.g., overlaps or coincides with) another field may be used in the alternative to derive a field similarity score.

In addition, or in alternative, to presenting the field similarity score, programmer 20 may output, for each of the first electrode combination and at least one of the one or more alternative electrode combinations, a visual representation of a stimulation field deliverable via the respective electrode combination. The visual representation may be a two dimensional (2D) graphical representation of the stimulation field and/or a three dimensional (3D) graphical representation of the stimulation field. The 2D representation may be shown one or more different views of the stimulation field, such a view along an axis of the lead and a side view orthogonal to the axis of the lead. Programmer 20 may provide the user to interact with the 3D representation and turn or move the 3D representation in space. In some examples, programmer 20 may display a distance grid or measurement markers on the stimulation field to allow the user to visualize differences in sizes of each stimulation field.

As discussed herein, programmer 20 may automatically select an alternative electrode combination based on appropriate metrics, such as preference given to reduced power consumption or the field similarity score. Alternatively, programmer 20 may present the information associated with each alternative electrode combination for user review via a user interface of programmer 20. Programmer 20 may then receive, via the user interface, a selection of one of the alternative electrode combinations and control delivery of electrical stimulation therapy to a patient according to the selected alternative electrode combination. For example, programmer 20 may generate one or more therapy programs that incorporate the selected alternative electrode combination for delivery of electrical stimulation therapy. In this manner, programmer 20 may control an IMD to deliver stimulation using the selected electrode combination. Programmer 20 may then transmit the therapy program (or only some stimulation parameters such as the selected electrode combination) to controller 14 to define stimulation therapy. An IMD, such as controller 14, may thus be configured to receive the selected alternative electrode combination and deliver the electrical stimulation therapy according to the selected alternative electrode combination.

The examples generally described herein are related to selecting one or more alternative electrode combinations for stimulation therapy in order to reduce power consumption while retaining field similarity to achieve a desired therapeutic outcome. In other examples, the processes described herein may be relevant to the selection of any stimulation parameters (e.g., current or voltage amplitude, pulse frequency, pulse width, duty cycle, monopolar or bipolar configurations, etc.) in order to determine other sets of stimulation parameters (e.g., one or more stimulation programs) that consume lower levels of power while also delivering stimulation fields providing therapeutic efficacy. For example, the system or a user may provide one or more constraints in the selection of stimulation parameters, such as which electrodes to use, which electrodes to avoid, desired current or voltage amplitudes, desired pulse frequency, desired pulse width and/or duty cycle, and/or VNA or VTA that is desired or to be avoided. Using these constraints, the system may automatically generate sets of stimulation parameters that satisfy these constraints and rank the sets of stimulation parameters by power consumption values and/or field similarity scores. The system may incorporate tissue resistances and various system resistances and/or impedances when calculating the power consumption values for each of these sets of stimulation parameters. In this manner, the system may generate sets of stimulation parameters without basing the parameters on an initial set of electrodes or initial electrode combination.

Example constraints for selection of stimulation parameters may include a request for a certain number of lowest power consuming sets of stimulation parameters that include electrodes no more than a certain distance (or number of electrodes) from a desired circumferential position on the lead. The system may require a certain constraints in order to generate usable stimulation parameters, such as minimums or maximums for one or more of current, voltage, pulse width, frequency, number of electrodes, volume of activated tissue, etc. These constraints may be defaults set by the system and/or user definable. Other example constraints may be a request for the lowest power consuming rings of electrodes, or lower power consuming electrode combinations and stimulation parameters with electrodes falling within a defined area of the lead. Constrains for stimulation field profiles, depth of tissue activation from the lead, or any other therapeutic constraints may also be used or even required to perform the request.

Figure 2A:
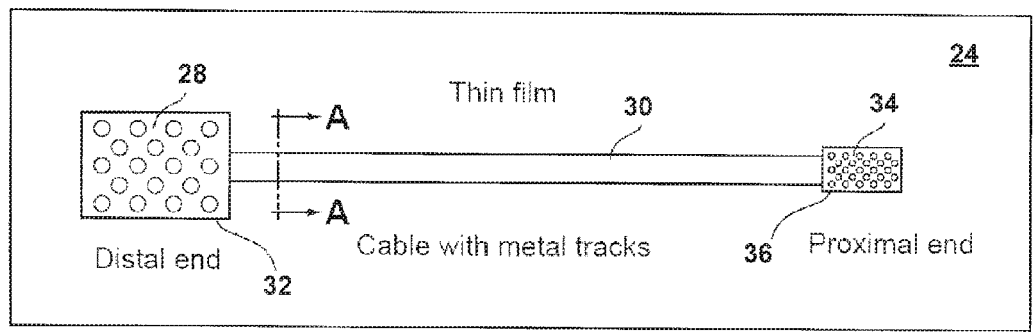
FIGS. 2A, 2B, and 2C are schematic diagrams of an example thin film, lead, and probe of a neurostimulation system for DBS.
Figure 2B:
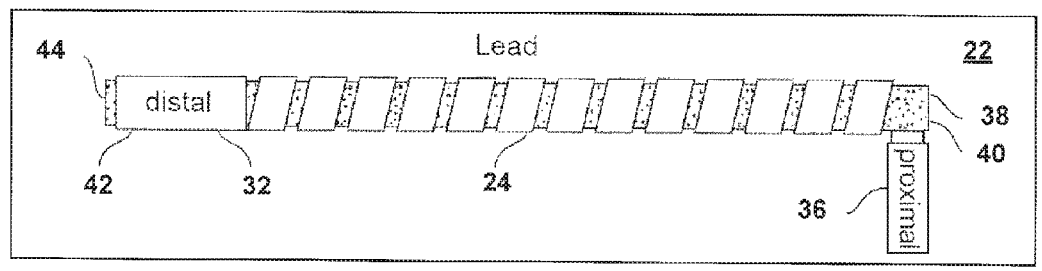
Figure 2C:
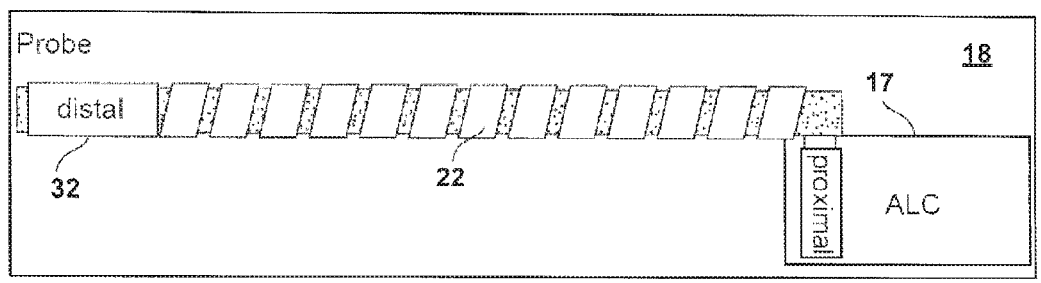
Figure 3:
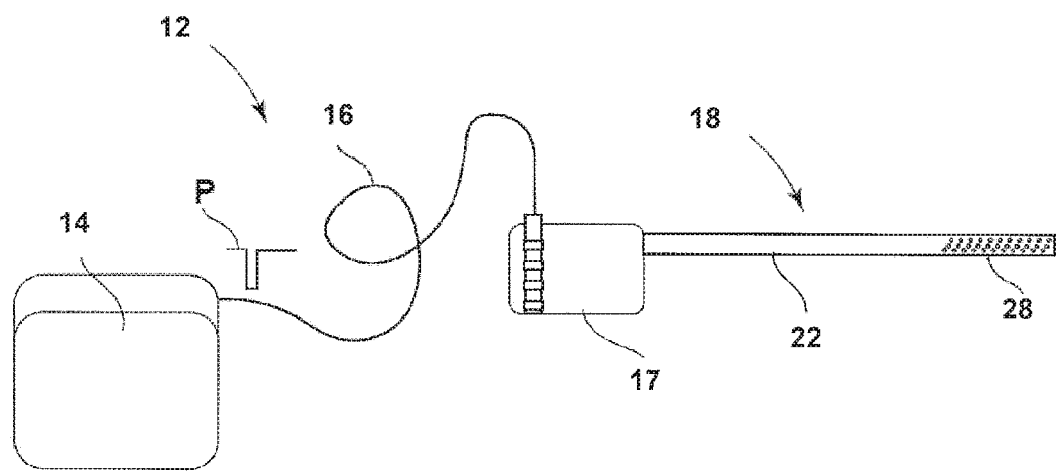
FIG. 3 is a conceptual drawing of an example system that delivers DBS.

FIGS. 2A, 2B, and 2C are schematic diagrams of an example thin film, lead, and probe of a neurostimulation system 10 for DBS. For example, FIG. 2A illustrates an example, thin film 24, FIG. 2B illustrates an example DBS lead 22, and FIG. 2C illustrates an example lead assembly 18 (e.g., a DBS probe) that include DBS lead 22 and a second module 17 (e.g., an active lead can (ALC) separate from controller 14). Second module 17 may include electronic means, such as a switch matrix, for addressing electrodes 28 disposed on the distal end 32 of the thin film 24. Electrodes 28 may be arranged at the distal end 42 of lead 22 and next to the distal tip 44 of the DBS lead 22. Electrodes 28 may be an example of a complex electrode array geometry with multiple levels of electrodes that are staggered in the circumferential direction. Although electrodes 28 include 18 electrodes, fewer or greater numbers of electrodes may be carried by lead 22. In one example, lead 22 may include 40 electrodes.

Lead 22 may include a carrier 38 for thin film 24. Carrier 38 may be sized and shaped to providing the mechanical configuration of DBS lead 22 and the thin film 24. In other words, thin film 24 may be wrapped around the circumference or diameter of carrier 38. Thin film 24 may include at least one electrically conductive layer and may be constructed of a biocompatible material. The thin film 24 may be assembled to carrier 38 and further processed to constitute lead 22.

The thin film 24 for a lead may be formed by a thin film product having a distal end 32, a cable 30 with metal tracks, and a proximal end 36. Proximal end 36 of the thin film 24 may be arranged at the proximal end 40 of lead 22 and is electrically connected to the second module 17. The second module 17 may include the switch matrix of the DBS steering electronics that selects different electrode combinations (e.g., selects which one or more electrodes are actively delivering an electrical signal) from electrodes 28. The distal end 32 comprises electrodes 28 for brain stimulation, for example. Proximal end 36 of thin film 24 includes interconnect contacts 34 for each metal track in the cable 30. The cable 30 comprises metal tracks or lines (not shown) to electrically connect each of distal electrodes 28 to a respective and designated proximal interconnect contact 34.

Second module 17 may include a switch matrix, or multiplexer, that is used to couple, or decouple, each electrode of electrodes 28 to one or more pulse generator lines and ground provided to second module 17 via a connecting cable (e.g., connecting cable 16 of FIG. 1 or 3). Second module 17 may also be electrically coupled to one or more ground electrodes. In some examples, second module 17 may include other control electronics, such as a microprocessor or other integrated circuitry, resistors, and capacitors. In still other examples, second module 17 may include one or more signal generators (e.g., one or more pulse generators) that are provided in addition to, or instead of, one or more of the pulse generators provided by controller 14. In other examples, the components of second module 17 may be incorporated into the housing of controller 14 such that a separate second module 17 is not necessary between controller 14 and electrodes 28.

FIG. 3 is a conceptual drawing of an example system 10 that delivers DBS. System 12 is described for brain applications, such as neurostimulation and/or neurorecording as a deep brain stimulation system 12 as shown in FIG. 1. System 12 may include at least one lead assembly 18 (e.g., a probe) for brain applications with stimulation and/or recording electrodes 28. In one example, forty electrodes 28 can be provided on the outer body surface at the distal end of the lead assembly 18. Controller 14 (e.g., a first module) may include one or more pulse generators that generate and supply neurostimulation pulses P to a second module 17 (e.g., an active lead can) by means of the connecting cable 16. A switch matrix of the second module 17 may direct the neurostimulation pulses P to the appropriate one or more electrodes (e.g., the electrode combination) for delivery to a patient. In some examples, controller 14 can be or include an implantable pulse generator. In other examples, controller 14 may be configured to simultaneously couple to two or more different second modules 17 and respective lead assemblies 18 via one or more connecting cables 16.

In the example of FIG. 3, system 12 may include controller 14 (e.g., a first module) that includes one or more pulse generators. Controller 14 may also include components such as a power supply, one or more processors, a memory, a communication unit for transmitting and/or receiving information from an external device, and other components. Second module 17 may include a switch matrix and, in some examples, one or more processors, a memory, and connectors for coupling lead 22 of FIG. 2 (where lead assembly 18 may include second module 17 and lead 22 carrying electrodes 28) and connecting cable 16. Second module 17 may have a housing encompassing the control electronics such as the switch matrix. In some examples, the housing may be electrically nonconductive such as an epoxy or polymer that insulates and protects the components of second module 17. The electrically nonconductive material may reduce encapsulation of the housing and/or insulate the brain from any interference caused by the components of second module 17.

Connecting cable 16 may connect controller 14 to second module 17. The plurality of electrodes 28 are disposed distal of second module 17 and on lead 22 of lead assembly 18. The control electronics for the plurality of electrodes 28 and the grounding electrode may provide at least one of neurostimulation and/or neurorecording via at least one electrode of the plurality of electrodes 28 and the grounding electrode. The control electronics are arranged in at least the first module 14 and the second module 17, but one or more additional modules may also include at least some of the control electronics. As described in FIG. 2A, lead assembly 18 may include lead 22 constructed of a thin film 24 carrying the plurality of electrodes 28. Lead 22 may be electrically coupled to the switch matrix of second module 17.

Figure 4:
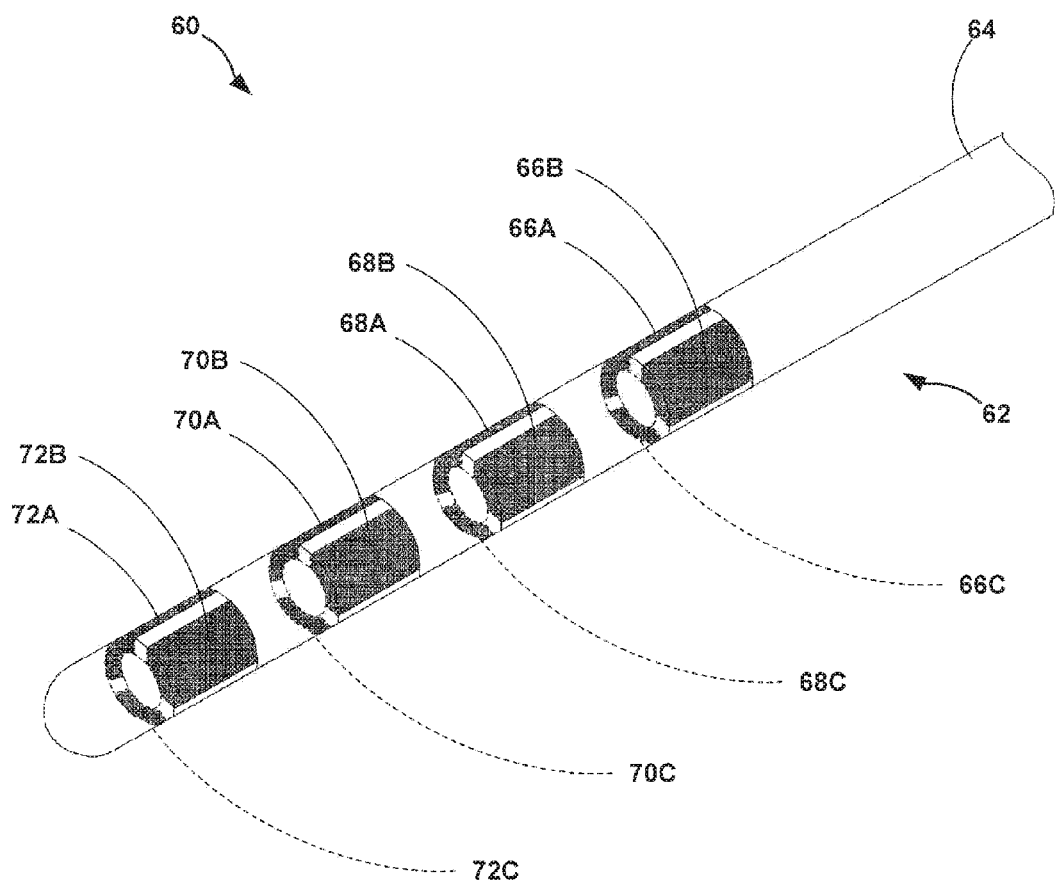
FIG. 4 is a conceptual drawing of another example lead having a complex electrode array geometry.

FIG. 4 is a conceptual drawing of another example lead 60 having a complex electrode array geometry. Lead 60 may be an alternative medical lead to lead 22 of FIGS. 2B and 3. Lead 60 includes distal end 62 showing a plurality of electrodes 66A-C, 68A-C, 70A-C, and 72A-C. As shown in FIG. 4, lead body 64 of lead 60 may be tubular in form and may have a substantially circular cross-section. However, lead body 64 of lead 60 may have any cross-sectional shape, such as rectangular, triangular, or other polygonal cross-sectional shapes in other examples, which may vary over the length of lead 60. An outer surface of lead body 64 may be formed from a biocompatible material such as, for example, polyurethane or silicone.

Distal portion 62 of lead 60 also includes segmented electrodes 66A-C (collectively "electrodes 66"), segmented electrodes 68A-C (collectively "electrodes 68"), 70A-C (collectively "electrodes 70"), and 72A-C (collectively "electrodes 72"). Each of electrodes 66, 68, 70, and 72 are levels of electrodes disposed at respective axial positions on lead body 64. Electrodes 66C, 68C, 70C, and 72C are located on the circumferential portion of lead 60 that is on the opposite side from the visible side of lead 60 in FIG. 4. The approximate locations of electrodes 66C, 68C, 70C, and 72C are outlined with dotted lines.

Electrodes 66, 68, 70, and 72 do not extend substantially around the entire periphery of the lead body 64. Each of electrodes 66, 68, 70, and 72 in the respective levels extend through arcs of 60 degrees, 80 degrees, 90 degrees, or as many as 119 degrees, although lesser or greater arcs may be used in other examples. Electrodes 66, 68, 70, and 72 in each respective level may be, but need not be, evenly spaced around the periphery of lead 60. Each of electrodes 66, 68, 70, and 72 can be made from an electrically conductive, biocompatible material, such as platinum iridium. In addition, one or more of 66, 68, 70, and 72 may function as sensing electrodes that monitor internal physiological signals of patient 1 (FIG. 1).

In the illustrated embodiment, lead 60 includes four levels of segmented electrodes 66, 68, 70, and 72, respectively. Each level of electrodes includes an electrode circumferentially aligned with respective electrodes in other levels. For example, electrodes 66A, 68A, 70A, and 72A are all circumferentially aligned with each other and at different axial positions on lead 60. However, in other examples, electrodes of different levels may be staggered, or not circumferentially aligned. Although each level includes three electrodes, a level of segmented electrodes may include two, four, five, six, or even more electrodes disposed at the same axial position. Example lead 60 includes four levels of electrodes, but fewer levels such as one, two, or three or more levels such as five, six, or more can be used in other examples. Each level may have the same number of segmented electrodes, but in other examples, different levels may have different number of electrodes.

In one example, lead 60 may include one or more ring electrodes in combination with one or more levels of multiple segmented electrodes. Ring electrodes may extend substantially around the entire periphery of lead 60. In some examples, multiple segmented electrodes may be used together as a ring electrode because they are configured to provide a stimulation field substantially similar to a full ring electrode. In some embodiments, the distances between each of the axial positions of each level (e.g., the positions of the levels of electrodes 66, 68, 70, and 72) may be approximately equal. However, the axial distance between electrodes may be varied between different levels of electrodes in other examples. Further, in some embodiments, although not illustrated in FIG. 4, lead 60 may be coupled to controller 14 (FIG. 1) or IMD 100 (FIG. 5) directly or via one or more lead extensions.

Figure 5:
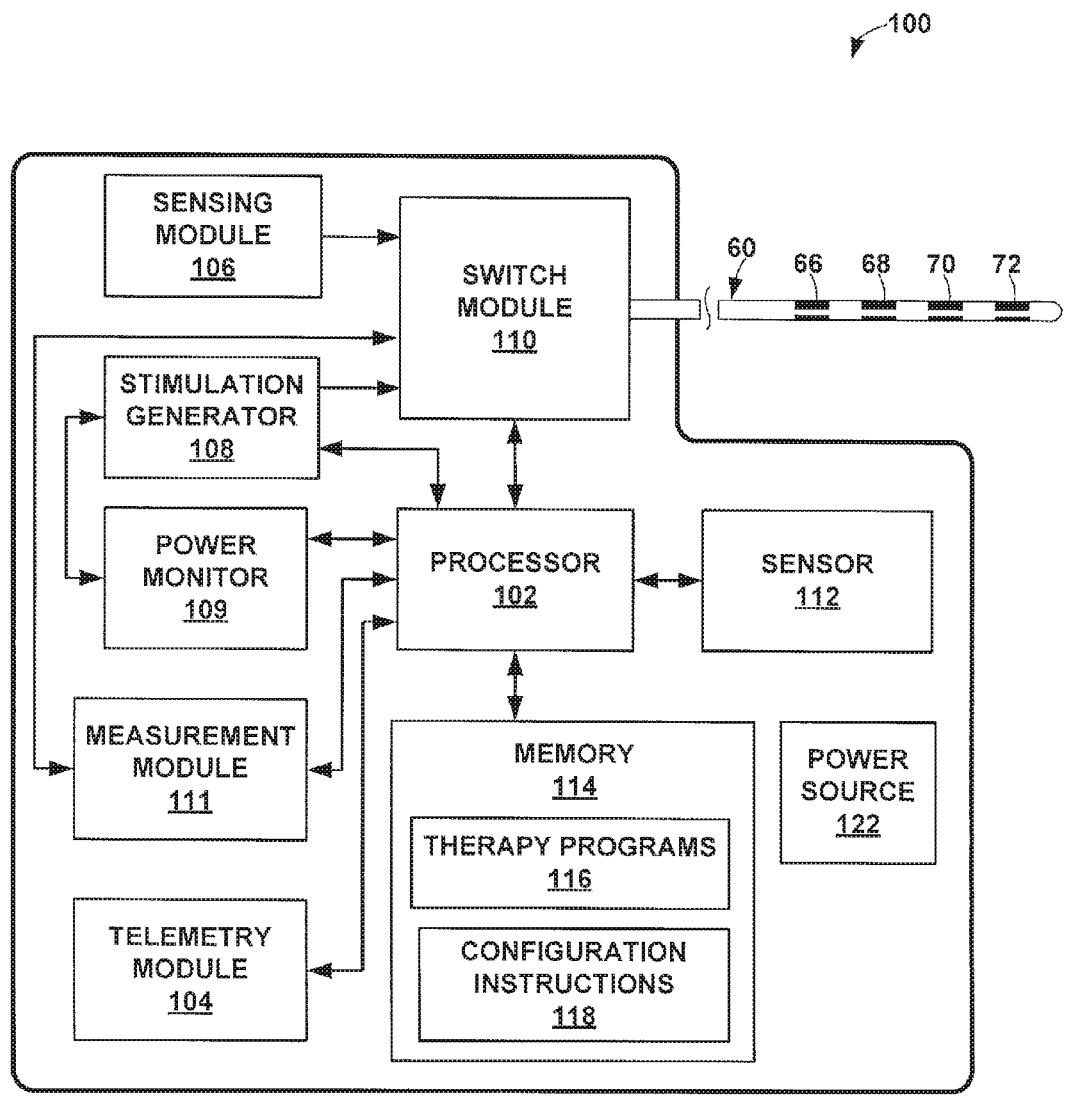
FIG. 5 is a functional block diagram of an example implantable medical device (IMD) configured to couple to one or more leads.

FIG. 5 is a functional block diagram of an example IMD 100 configured to couple to one or more leads 60. IMD 100 may be similar to controller 14 of FIG. 1 and may include at least some functionality of second module 17 (FIG. 3), however, second module 17 may not be located separate from IMD 100. Each of these modules include electrical circuitry configured to perform the functions described herein. In the example shown in FIG. 5, IMD 100 includes processor 102, memory 114, stimulation generator 108, power monitor 109, measurement module 111, sensing module 106, switch module 110, telemetry module 104, sensor 112, and power source 122. Memory 114 may include any volatile or non-volatile media, such as a random access memory (RAM), read only memory (ROM), non-volatile RAM (NVRAM), electrically erasable programmable ROM (EEPROM), flash memory, and the like. Memory 114 may store computer-readable instructions that, when executed by processor 102, cause IMD 100 to perform various functions. Memory 114 may be a storage device or other non-transitory medium.

In the example shown in FIG. 5, memory 114 stores therapy programs 116 and configuration instructions 118 in common or separate memories or areas within memory 114. Each stored therapy program 116 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Configuration instructions 118 may include rules, algorithms, data, or any other information related to determining alternative electrode combinations, calculating power consumption values and stimulation field similarity scores, and selecting an alternative electrode combination for therapy. For example, configuration instructions 118 may include one or more algorithms defining how to generate different alternative electrode combinations based on an initial electrode combination. Configuration instructions 118 may also include instructions regarding whether processor 102 should automatically select an alternative electrode combination or present alternative electrode combinations to a user for selection. In some examples, configuration instructions 118 may only include some information necessary to determine and select alternative electrode combinations because programmer 20 or another device may perform some or all of the steps in the process.

Stimulation generator 108, under the control of processor 102, generates stimulation signals for delivery to patient 1 via one or more electrodes defined by a selected electrode combination. An example range of electrical stimulation parameters believed to be effective in DBS to manage a movement disorder of patient include:

1. Frequency: between approximately 100 Hz and approximately 500 Hz, such as approximately 130 Hz.
2. Voltage Amplitude: between approximately 0.1 volts and approximately 50 volts, such as between approximately 1 volts and approximately 10 volts, or approximately 3 volts.
3. Current Amplitude: In a current-controlled system, the current amplitude, assuming a lower level impedance of approximately 500 ohms, may be between approximately 0 milliamps to approximately 100 milliamps, such as between approximately 0.1 milliamps and approximately 40 milliamps in some examples. In other examples, the current amplitudes may be between approximately 0.1 milliamps and approximately 10 milliamps, or approximately 3 milliamps in one example. However, in some examples, the impedance may range between about 200 ohms and about 2 kiloohms.
4. Pulse Width: between approximately 10 microseconds and approximately 5000 microseconds, such as between approximately 10 microseconds and approximately 500 microseconds.

Accordingly, in some examples, stimulation generator 108 generates electrical stimulation signals in accordance with the electrical stimulation parameters noted above. Other ranges of therapy parameter values may also be useful, and may depend on the target stimulation site within patient 1. While stimulation pulses are described, stimulation signals may be of any form, such as continuous-time signals (e.g., sine waves) or the like.

Power monitor 109 may be connected to stimulation generator 108 and include circuitry configured to monitor, or measure, power consumption by one or more current sources of stimulation generator 108. In this manner, power monitor 109 may provide information to processor 102 regarding the power consumption for each alternative electrode combination or overall set of stimulation parameters used to deliver electrical stimulation at any given time. Measurement module 111 may also be connected to switch module 110 (or a switch matrix) and include circuitry configured to measure resistance and/or impedance associated with each electrode and/or each electrode combination or each load and/or load combinations connected to stimulation generator 108. For example, measurement module 111 may measure resistances of each electrode and provide the resistances to processor 102 for generation of the R-matrix of all electrodes of lead 60. The R-matrix and/or Z-matrix may be used to calculate the power consumption that occurs within the tissue of the patient and/or the tissue of the patient and all other electrical components between the stimulation generator and the tissue, such that the total power consumption for a system delivering stimulation therapy would include the power consumption by the tissue and the power consumption that occurs within the system (e.g., within the stimulation generator, between the tissue and the stimulation generator, and other electrical components).

Processor 102 may control measurement module 111 to measure the R-matrix and/or Z-matrix, or any other representation of tissue resistance and/or load impedance, once or several times over the course of stimulation therapy. For example, processor 102 may initially control measurement module 111 to measure the R-matrix after implantation of lead 60 and prior to selecting stimulation parameters for stimulation therapy. Since the composition of tissue around lead 60 and the electrodes thereof may change over time (e.g., due to encapsulation, scar tissue, etc.), processor 102 may periodically re-measure the R-matrix according to a predetermined schedule and/or in response to detected events. Detected events may include a visit by the patient to a clinic, a replaced implantable component, the loss or failure of an electrode (or corresponding switch or conductor), or even a traumatic accident endured by the patient that may have moved the lead relative to tissue. In this manner, the updated R-matrix may provide for more accurate power consumption values and more accurate stimulation field determination with associated similarities of alternative electrode combinations or other sets of stimulation parameters.

The R-matrix or Z-matrix, as referred to herein, may describe the resistance, or impedance, of tissue for a specific patient within which the electrodes are implanted. It may also describe the load impedance (e.g., electrical components between tissue and stimulation generator plus the tissue itself) connected to the each current source of the stimulation generator. In this manner, the R-matrix or Z-matrix may provide specific information regarding the tissue-electrode interface and current path through tissue between electrodes and these electrodes and the stimulation generator. In one example, the R-matrix or Z-matrix may be calculated applying a test stimulation current between two electrodes or between an electrode and a housing of IMD 100, for example, measuring the resulting excitation voltage, and deriving an impedance between the electrodes based on the test stimulation current and the resulting excitation voltage. This process may be repeated for all different electrodes, in some examples, or in only some electrode and extrapolated to other electrodes, in other examples. The test stimulation currents may be at sub-threshold levels (e.g., 0.1 mA) in some examples to avoid neuron activation during impedance measurement, and the resulting measured resistances may be extrapolated up to typical therapeutic currents (e.g., 3.0 mA) to provide an R-matrix or Z-matrix representative of actual therapy delivery. In other examples, the R-matrix may be determined using test stimulation currents at normal therapeutic current levels or using actual therapeutic stimulation during therapy. Example methods for determining the R-matrix or Z-matrix for tissue of the patient are described in Patent Cooperation Treaty Publication No. WO 2011/107917 A1 by Emil Toader et al., and entitled "Method and System for Determining Settings for Deep Brain Stimulation," the entire content of which is incorporated herein by reference.

Processor 102 may include any one or more of a microprocessor, a controller, a digital signal processor (DSP), an application specific integrated circuit (ASIC), a field-programmable gate array (FPGA), discrete logic circuitry, and the functions attributed to processor 102 herein may be embodied as firmware, hardware, software or any combination thereof. Processor 102 controls stimulation generator 108 according to therapy programs 116 stored in memory 114 to apply particular stimulation parameter values specified by one or more of programs, such as amplitude, pulse width, and pulse rate.

In the example shown in FIG. 5, the set of electrodes 66, 68, 70, and 72 of lead 60 are coupled to switch module 110 for delivery of electrical stimulation. In other examples, two or more leads may be coupled to switch module 110 with similar or varying configurations of electrodes. Processor 102 also controls switch module 110 to apply the stimulation signals generated by stimulation generator 108 to selected combinations of electrodes 66, 68, 70, and 72. In particular, switch module 110 may couple stimulation signals to selected conductors within lead 60, which, in turn, deliver the stimulation signals across selected electrodes 66, 68, 70, and 72. Switch module 110 may be a switch array, switch matrix, multiplexer, or any other type of switching module configured to selectively couple stimulation energy to selected electrodes 66, 68, 70, and 72 and to selectively sense bioelectrical brain signals with selected electrodes 66, 68, 70, and 72. Hence, stimulation generator 108 is coupled to electrodes 66, 68, 70, and 72 via switch module 110 and conductors within lead 60. In some examples, however, IMD 100 does not include switch module 110.

Stimulation generator 108 may be a single channel or multi-channel stimulation generator. In particular, stimulation generator 108 may be capable of delivering a single stimulation pulse, multiple stimulation pulses, or a continuous signal at a given time via a single electrode combination or multiple stimulation pulses at a given time via multiple electrode combinations. In some examples, however, stimulation generator 108 and switch module 110 may be configured to deliver multiple channels on a time-interleaved basis. For example, switch module 110 may serve to time divide the output of stimulation generator 108 across different electrode combinations at different times to deliver multiple programs or channels of stimulation energy to patient 1.

Although sensing module 106 is incorporated into a common housing with stimulation generator 108 and processor 102 in FIG. 5, in other examples, sensing module 106 may be in a separate housing from IMD 100 and may communicate with processor 102 via wired or wireless communication techniques. Example bioelectrical brain signals include, but are not limited to, a signal generated from local field potentials within one or more regions of the brain. EEG and ECoG signals are examples of local field potentials that may be measured within the brain. However, local field potentials may include a broader genus of electrical signals within the brain of patient 1.

Sensor 112 may include one or more sensing elements that sense values of a respective patient parameter. For example, sensor 112 may include one or more accelerometers, optical sensors, chemical sensors, temperature sensors, pressure sensors, or any other types of sensors. Sensor 112 may output patient parameter values that may be used as feedback to control delivery of therapy. IMD 100 may include additional sensors within the housing of IMD 100 and/or coupled via lead 60 or other leads. In addition, IMD 100 may receive sensor signals wirelessly from remote sensors via telemetry module 104, for example. In some examples, one or more of these remote sensors may be external to patient (e.g., carried on the external surface of the skin, attached to clothing, or otherwise positioned external to the patient). Each of the sensor signals may be calibrated by identified patient behavior from video information and incorporated in the feedback control of therapy.

Telemetry module 104 supports wireless communication between IMD 100 and an external programmer 20 or another computing device under the control of processor 102. Processor 102 of IMD 100 may receive, as updates to programs, values for various stimulation parameters such as amplitude and/or alternative electrode combination(s), from programmer 20 via telemetry module 104. The updates to the therapy programs may be stored within therapy programs 116 portion of memory 114. Telemetry module 104 in IMD 100, as well as telemetry modules in other devices and systems described herein, such as programmer 20, may accomplish communication by radiofrequency (RF) communication techniques. In addition, telemetry module 104 may communicate with external medical device programmer 20 via proximal inductive interaction of IMD 100 with programmer 24. Accordingly, telemetry module 104 may send information to external programmer 24 on a continuous basis, at periodic intervals, or upon request from IMD 100 or programmer 24.

Power source 122 delivers operating power to various components of IMD 100. Power source 122 may include a small rechargeable battery, a non-rechargeable battery, and/or another type of energy storage device such as one or more super capacitors, and a power generation circuit to produce the operating power. Recharging may be accomplished through proximal inductive interaction between an external charger and an inductive charging coil within IMD 100. In some examples, power requirements may be small enough to allow IMD 100 to utilize patient motion and implement a kinetic energy-scavenging device to trickle charge a rechargeable battery. In other examples, traditional batteries may be used for a limited period of time.

Figure 6:
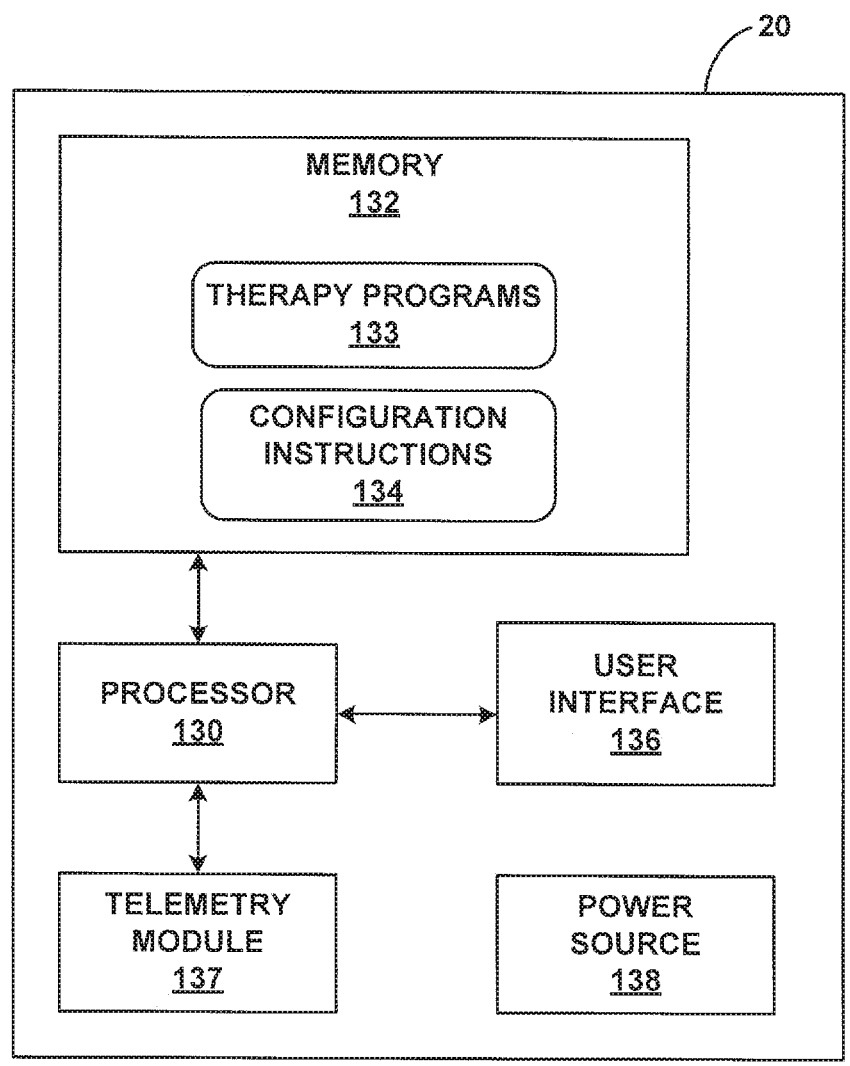
FIG. 6 is a functional block diagram of an example external programmer for an IMD.

FIG. 6 is a functional block diagram of an example external programmer 20 for an IMD such as IMD 100 or controller 14. Although programmer 20 may generally be described as a hand-held device, programmer 20 may be a larger portable device or a more stationary device. In addition, in other examples, programmer 20 may be included as part of an external charging device or include the functionality of an external charging device. As illustrated in FIG. 6, programmer 20 may include a processor 130, memory 132, user interface 136, telemetry module 137, and power source 138. Memory 132 may store instructions that, when executed by processor 130, cause processor 130 and external programmer 20 to provide the functionality ascribed to external programmer 20 throughout this disclosure. For example, configuration instructions 134 in memory 132 may cause programmer 20 to determine alternative electrode combinations and receive user input selecting an alternative electrode combination to reduce power consumption of stimulation therapy.

In general, programmer 20 comprises any suitable arrangement of hardware, alone or in combination with software and/or firmware, to perform the techniques attributed to programmer 20, and processor 130, user interface 136, and telemetry module 137 of programmer 20. In various examples, programmer 20 may include one or more processors, such as one or more microprocessors, DSPs, ASICs, FPGAs, or any other equivalent integrated or discrete logic circuitry, as well as any combinations of such components. Programmer 20 also, in various examples, may include a memory 132, such as RAM, ROM, PROM, EPROM, EEPROM, flash memory, a hard disk, a CD-ROM, comprising executable instructions for causing the one or more processors to perform the actions attributed to them. Moreover, although processor 130 and telemetry module 137 are described as separate modules, in some examples, processor 130 and telemetry module 137 are functionally integrated. In some examples, processor 130 and telemetry module 137 correspond to individual hardware units, such as ASICs, DSPs, FPGAs, or other hardware units.

Memory 132 (e.g., a storage device) may store instructions that, when executed by processor 130, cause processor 130 and programmer 20 to provide the functionality ascribed to programmer 20 throughout this disclosure. For example memory 132 may include instructions that cause processor 130 to obtain a parameter set from memory, select a spatial electrode movement pattern, or receive a user input and send a corresponding command to IMD 14, or instructions for any other functionality. In addition, memory 132 may include a plurality of therapy programs 133 (similar to therapy programs 116 of FIG. 5), where each therapy program includes a parameter set that defines stimulation therapy.

Configuration instructions 134 may be similar to configuration instructions 118 of IMD 100 and may include rules, algorithms, data, or any other information related to determining alternative electrode combinations, calculating power consumption values and stimulation field similarity scores, and selecting an alternative electrode combination for therapy. For example, configuration instructions 134 may include one or more algorithms defining how to generate different alternative electrode combinations based on an initial electrode combination. Configuration instructions 134 may also include instructions regarding whether processor 130 should automatically select an alternative electrode combination or present alternative electrode combinations to a user for selection. For example, configuration instructions 134 may define how power consumption values, field similarity scores, and/or visual representations of stimulation fields are determined or calculated and/or generated for presentation to a user. In some examples, configuration instructions 134 may only include some information necessary to determine and select alternative electrode combinations because programmer 20 or another device may perform some or all of the steps in the process.

User interface 136 may include a button or keypad, lights, a speaker for voice commands, a display, such as a liquid crystal (LCD), light-emitting diode (LED), or organic light-emitting diode (OLED). In some examples the display may be a touch screen. User interface 136 may be configured to display any information related to the delivery of stimulation therapy, alternative electrode combinations, or any other such information. User interface 136 may also receive user input via user interface 136. The input may be, for example, in the form of pressing a button on a keypad or selecting an icon from a touch screen.

Telemetry module 137 may support wireless communication between controller 114 or IMD 14 and programmer 20 under the control of processor 130. Telemetry module 137 may also be configured to communicate with another computing device via wireless communication techniques, or direct communication through a wired connection. In some examples, telemetry module 137 may be substantially similar to telemetry module 104 of IMD 100 described herein, providing wireless communication via an RF or proximal inductive medium. In some examples, telemetry module 137 may include an antenna, which may take on a variety of forms, such as an internal or external antenna.

Examples of local wireless communication techniques that may be employed to facilitate communication between programmer 20 and controller 14 or IMD 100 include RF communication according to the 802.11 or Bluetooth specification sets or other standard or proprietary telemetry protocols. In this manner, other external devices may be capable of communicating with programmer 20 without needing to establish a secure wireless connection. As described herein, telemetry module 137 may be configured to transmit a spatial electrode movement pattern or other stimulation parameter values to controller 14 or IMD 100 for delivery of stimulation therapy.

Figure 7:
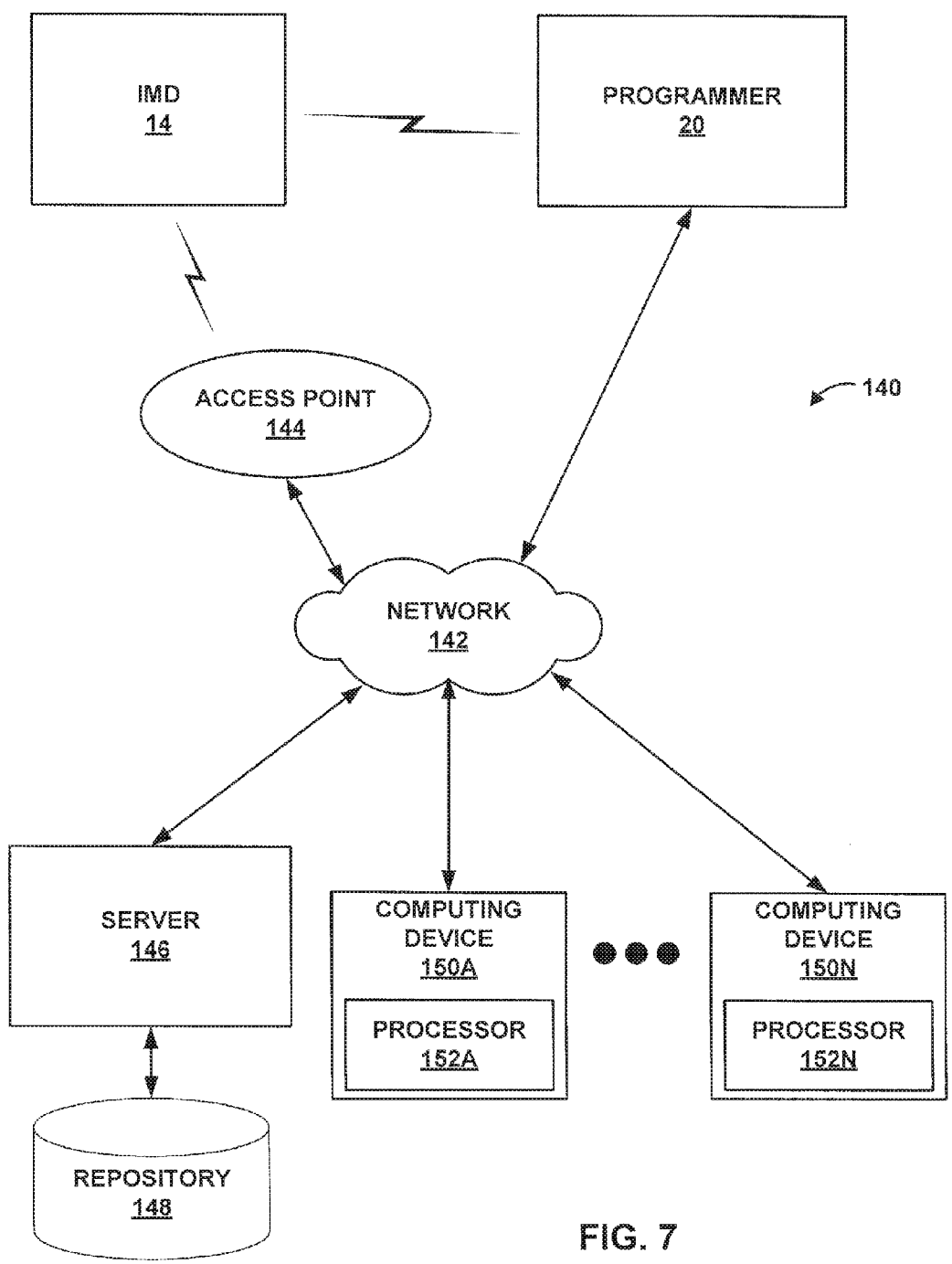
FIG. 7 is a conceptual diagram of an example distributed system that operates over a network.

FIG. 7 is a conceptual diagram of an example distributed system 140 that operates over a network. As shown in FIG. 7, system 140 that includes networked server 146 coupled to IMD 14 (and/or controller 14) and one or more computing devices 150 via network 142. Server 146 (e.g., a networked external computing device) and one or more computing devices 150A-150N that are coupled to the IMD 14 and programmer 20 via a network 142. Network 142 may be generally used to transmit sensed data and/or information related to determining and/or selecting alternative electrode combinations. For example, programmer 20 may send alternative electrode combinations and the initial electrode combination to sever 146 in order for server 146 to calculate data such as power consumption values, field similarity scores, and/or 2D or 3D graphical representations of the stimulation fields. Such information may be computationally intensive and benefit from offloading from programmer 20 and or IMD 14. The distributed computing of system 140 may be used for any process described herein.

In some examples, the information transmitted by IMD 14 may allow a clinician or other healthcare professional to monitor patient 1 remotely. In some examples, IMD 14 may use a telemetry module to communicate with programmer 20 via a first wireless connection, and to communicate with access point 144 via a second wireless connection, e.g., at different times. In the example of FIG. 7, access point 144, programmer 20, server 146 and computing devices 150A-150N are interconnected, and able to communicate with each other through network 142. In some cases, one or more of access point 144, programmer 20, server 146 and computing devices 150A-150N may be coupled to network 142 via one or more wireless connections. IMD 14, programmer 20, server 146, and computing devices 150A-150N may each comprise one or more processors, such as one or more microprocessors, DSPs, ASICs, FPGAs, programmable logic circuitry, or the like, that may perform various functions and operations, such as those described herein.

Access point 144 may comprise a device that connects to network 142 via any of a variety of connections, such as telephone dial-up, digital subscriber line (DSL), or cable modem connections. In other examples, access point 144 may be coupled to network 142 through different forms of connections, including wired or wireless connections. In some examples, access point 144 may be co-located with patient 14 and may comprise one or more programming units and/or computing devices (e.g., one or more monitoring units) that may perform various functions and operations described herein. For example, access point 144 may include a home-monitoring unit that is co-located with patient 14 and that may monitor the activity of IMD 14. In some examples, server 146 or computing devices 150 may control or perform any of the various functions or operations described herein.

In some cases, server 146 may be configured to provide a secure storage site for archival of video information, therapy parameters, patient parameters, or other data that has been collected and generated from IMD 14 and/or programmer 20. Network 142 may comprise a local area network, wide area network, or global network, such as the Internet. The system of FIG. 7 may be implemented, in some aspects, with general network technology and functionality similar to that provide by the Medtronic CareLink® Network developed by Medtronic, Inc., of Minneapolis, Minn.

Figure 8:
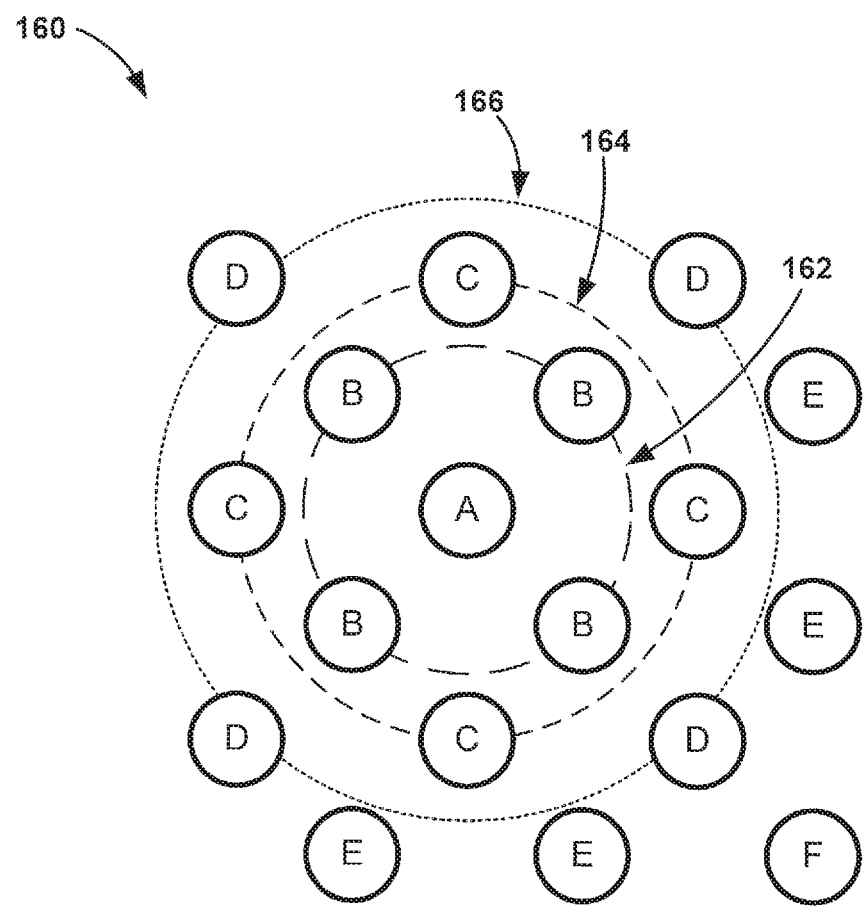
FIG. 8 is a conceptual diagram of example alternative electrode combinations selected based on the distance of other electrodes to an electrode of the initial electrode combination.

FIG. 8 is a conceptual diagram of example alternative electrode combinations selected based on the distance of other electrodes to an electrode of the initial electrode combination. As shown in FIG. 8, electrodes 160 is a set of 18 electrodes in a staggered configuration such as electrodes 28 of FIG. 2A. Alternative electrode combinations may be based on an initial electrode combination and the distance from an electrode of an initial electrode combination to adjacent electrodes.

In one example, programmer 20, for example, may start with an initial electrode combination and add electrodes to generate alternative electrode combinations. In one example, the distances may be the Euclidian distance based on an "unwrapping" or "unrolling" of the complex electrode array geometry as shown in FIG. 8. Electrode A may be the single electrode of the initial electrode combination. Adjacent to electrode A are four electrodes B that are each the same distance 162 from electrode A. Programmer 20 may thus define a first alternative electrode combination as electrodes A and B (e.g., 5 electrodes). At the next distance 164 that is further from electrode A, programmer 20 may add electrodes C to determine the second alternative electrode combination as electrodes A, B, and C (e.g., 9 electrodes). At the next distance 166 that is again further from electrode A, programmer 20 may add electrodes D to determine the third alternative electrode combination as electrodes A, B, C, and D (e.g., 13 electrodes). By iteratively adding electrodes at further distances from electrode A, programmer 20 may have determined some electrode combinations with lower impedances and/or power consumption values than just electrode A.

In the example of FIG. 8, the distances 162, 164, and 166 are calculated from the center of electrode A to the center of the other respective electrodes. However, in other examples, the distance between electrodes may be calculated from the middle of the initial electrode to the nearest edge of another electrode, from the nearest edges between two electrodes, or according to any other algorithm. Distances 162, 164, and 166 are calculated as Euclidian distances. Other methods for determining distances may be used in other examples. For example, on a cylindrical lead, programmer 20 may calculate the arc distance around the surface of the lead from one electrode to another electrode. In other examples, programmer 20 may model the expected average path of electrical current through tissue from the initial electrode to alternative electrodes. In other words, the electrical path may arc at some distance away from the surface of the lead. Programmer 20 may use the expected average path of the electrical current as the distance between two electrodes.

As shown in the example of FIG. 8, all electrodes at each equidistant location from electrode A may be used in order to maintain the symmetry of the stimulation field to the stimulation field of the initial electrode combination. Programmer 20 may continue to determine additional alternative electrode combinations if further electrodes of the complex electrode array geometry are available or until a symmetrical group of electrodes can no longer be added. However, additional electrodes will continue to alter the stimulation field. In other examples, electrodes added for a single alternative electrode combination may not all be at exactly equidistant from the initial electrode. Instead, programmer 20 may use two or more electrodes within a range of distances of the initial electrode. Using a distance range may be appropriate for electrode arrays that are unsymmetrical or have varied distances between adjacent electrodes. Such a range may also be useful when the initial electrode combination includes two or more electrodes.

The example of FIG. 8 illustrates an initial electrode combination of one electrode. However, the initial electrode combination may include two or more electrodes. For multiple electrodes in the initial electrode combination, subsequent alternative electrode combinations may be determined by adding the next closest available electrodes. The new alternative electrode combinations may add electrodes to generally maintain the original spatial shape of the initial electrode combination or otherwise attempt to maintain the stimulation field shape. In other examples, programmer 20 may determine one or more alternative electrode combinations by shifting one or more electrodes in one direction from the initial electrode combination. In this manner, alternative electrode combinations may be determined via asymmetrical shifting of electrodes, addition of electrodes, or even subtraction of electrodes. Alternative electrode combinations may include fewer electrodes than an initial electrode combination if the electrodes of the alternative electrode combination have a lower collective impedance than the electrodes of the initial electrode combination. This may occur based on differences in tissue resistance surrounding the electrodes of the lead, for example.

Electrodes 160 are shown as staggered levels of electrodes. However, different electrode arrays may have different configurations of electrodes. For example, electrodes 160 may be shown in aligned rows and columns that represent lead 60 of FIG. 4. Any type of electrode configuration may be shown in such a manner.

In some examples, programmer 20 may continue to generate alternative electrode combinations until the field similarity score drops below a predetermined threshold. For example, programmer 20 may calculate a field similarity score for a newly determined alternative electrode combination with respect to the initial electrode combination. If the field similarity score is below a threshold of 80%, for example, programmer 20 may stop generating any additional alternative electrode combinations because further additions of electrodes will likely further decrease the field similarity score. Programmer 20 may or may not discard any alternative electrode combinations that have a field similarity score below the predetermined threshold. The predetermined threshold may be set to any desired threshold, such as about 50%, 60%, 70%, 80%, or 90%, or any other threshold lower, higher, or in between these thresholds. In some examples, the predetermined threshold for the field similarity score may be used as one input for determining how many alternative electrode combination are generated. Programmer 20 may, for example, generate at least a predetermined number of alternative electrode combinations even if one or more of the alternative electrode combinations have a field similarity score below the predetermined threshold. In other examples, programmer 20 may only generate the predetermined number of alternative electrode combinations (e.g., two, three, four, five, or more) even if the field similarity scores are still above the predetermined threshold.

When calculating and/or measuring the power consumption values and/or stimulation fields for the initial electrode combination and the alternative electrode combinations, programmer 20 may assume the same stimulation parameters (e.g., current or voltage amplitude, pulse width, pulse frequency, etc.) for each of the electrodes across all electrode combinations. In the alternative, programmer 20 may use one or more different stimulation parameters between different alternative electrode combinations or even one or more different stimulation parameters for different electrodes within the same alternative electrode combination. For example, more centrally located electrodes of an alternative electrode combination may use higher current or voltage amplitudes than more peripheral electrodes. In other examples, peripheral electrodes of the alternative electrode combinations may have higher current or voltage amplitudes than more centrally located electrodes of the electrode combination. These different stimulation parameter values may allow for further reduction in power consumption and/or more similar stimulation fields when compared to the initial electrode combinations.

In some examples, programmer 20 may assume that all electrodes 160 of the complex electrode array are available for stimulation and inclusion in alternative electrode combinations. However, one or more electrodes may not function as intended due to conductor fracture between an electrode and the stimulation generator, switch matrix error or failure, or even excessive encapsulation that raises the impedance of an electrode. Controller 14 or IMD 100 may periodically test each electrode and determine whether or not each electrode is still functional or available to deliver stimulation therapy. This periodic testing may include re-determining, re-measuring or re-calculating the electrode resistance (e.g., R-matrix) or impedance (e.g., Z-matrix) for all electrodes, electronics, and tissue associated with the system. Programmer 20 may use the results of the test (or resistance/impedance matrix) when determining alternative electrode combinations. Good electrodes may be available, or alternatively, bad electrodes may be restricted from being used in an electrode combination. Therefore, when determining alternative electrode combinations, programmer 20 may only use functioning electrodes for each alternative electrode combination.

The example of FIG. 8 may be used when the initial electrode combination and alternative electrode combinations are used in a monopolar or unipolar configuration. In a monopolar or unipolar configuration, one or more ground electrodes may be located on controller 14 of IMD 100 (e.g., carried on the implant housing), on a portion of the lead or connection between the IMD and the lead, or as part of second module 17. In other examples, one or more electrodes (e.g., one or more levels of a complex electrode array geometry) that are not selected as active electrodes may be utilized as a ground electrode that sinks current that is sourced from the active electrodes. In other examples, bipolar configurations of electrodes may be used. In a bipolar configuration, alternative electrode combinations may be determined for one or more of the initial anode and/or cathode electrodes of the initial electrode combination.

As described herein, programmer 20 may calculate various metrics to characterize the alternative electrode combinations. Programmer 20 may calculate a power consumption value and a field similarity score for each of the alternative electrode combinations. Table 1 provided below provides information for each of the initial (or original) electrode combination and the determined alternative electrode combinations. For example, Table 1 includes the Euclidian distance, Power consumption, Power consumption reduction percentage, and Sorensen-Dice field similarity score for each electrode combination. Both of the power consumption and power consumption reduction percentage may be referred to as a power consumption reduction value.

TABLE 1

| Electrode configuration | Euclidean distance [units] | Power consumption [mW] | Power consumption Reduction | Sørensen-Dice |
|---|---|---|---|---|
| Original (1 contact) | 0.0 | 12.5 | 0% | 100% |
| Configuration 1 (5 contacts) | 1.4 | 3.8 | 70% | 93% |
| Configuration 2 (9 contacts) | 2.0 | 2.7 | 78% | 88% |
| Configuration 3 (13 contacts) | 2.8 | 2.1 | 83% | 81% |

In the example of Table 1 and FIG. 8, the "Original" electrode combination corresponds to electrode A, "Configuration 1" corresponds to electrodes A and B, "Configuration 2" corresponds to electrodes A, B, and C, and "Configuration 3" corresponds to electrodes A, B, C, and D. The Euclidian distance represents the distances 162, 164, and 166, respectively. The Power consumption may be the absolute power consumption based on the common current (e.g., 1.5 mA) and the total impedance of the electrodes in each electrode combination, and the impedance of the remainder of the system (which may include additional electronics and/or tissue impedances associated with each electrode). The Power consumption reduction percentage may be the percentage decrease of the total power consumption for the alternative electrode combination as compared to the initial electrode combination. The Sorensen-Dice field similarity score may be the numerical value attributed to the similarity of the stimulation field from the alternative electrode combination to the stimulation field from the initial electrode combination.

The information in Table 1 may be output and presented to a user as a representation of the alternative electrode combination. A user may review the information of Table 1 and base the selection of one of the alternative electrode combination on the data of Table 1. If programmer 20, controller 14, IMD 100, or any other device automatically selects an alternative electrode combination for stimulation therapy, programmer 20 may still present the information for the selected alternative electrode combination or even all of the possible alternative electrode combinations for the user to review. Programmer 20 may require the user to confirm the automated selection of the alternative electrode combination, or programmer 20 may present a mechanism for the user to reject the selected alternative electrode combination and receive user selection for a different alternative electrode combination or even the initial electrode combination if none of the alternative electrode combinations are acceptable to the user.

The alternative electrode combinations may be ranked in Table 1 according to a variety of factors. In one example, the alternative electrode combination may be ranked according to decreasing field similarity scores. In other examples, the alternative electrode combinations may be ranked based in decreasing power consumption values, increasing number of electrodes, or any other variations. In some examples, alternative electrode combinations may be displayed with information regarding patient feedback for the various alternative electrode combinations if the combination has been used and reviewed by the patient. In this manner, programmer 20 may display feedback scores from the patient that may or may not correspond to the calculated field similarity score.

Figure 9:
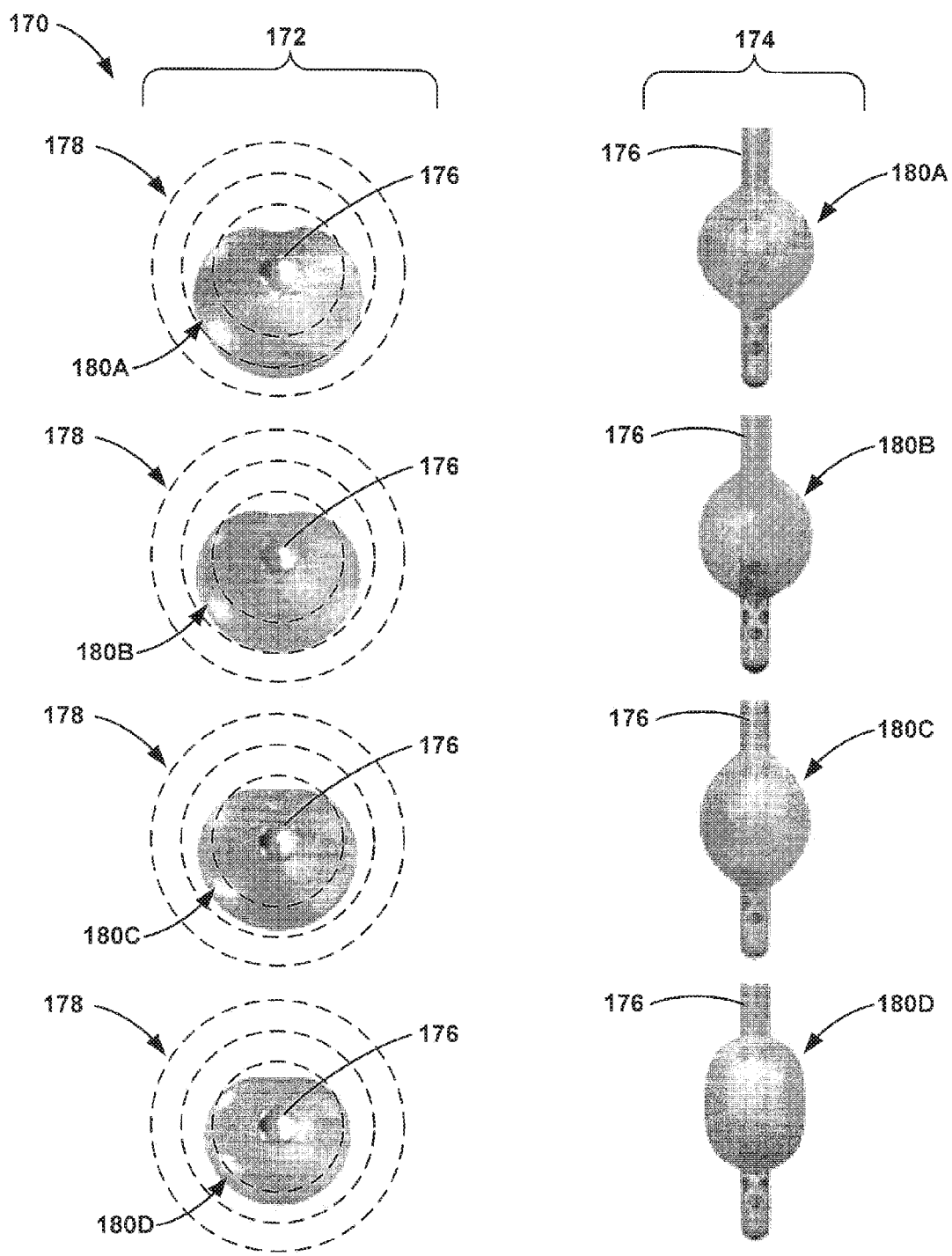
FIG. 9 is a conceptual diagram of example stimulation fields deliverable from alternative electrode combinations.

FIG. 9 is a conceptual diagram of example stimulation fields deliverable from alternative electrode combinations. As shown in FIG. 9, programmer 20 (or any other device described herein) has generated and presented graphical representations of the stimulation fields deliverable by each of the initial electrode combination and the alternative electrode combinations discussed in FIG. 8. Representation 170 may be a representation of the stimulation fields that can be output and displayed to a user via programmer 20, for example. Axial views 172 include the axial views of each of stimulation fields 180A, 180B, 180C, and 180D (collectively "stimulation fields 180") with respect to lead 176. With respect to the electrode combinations of FIG. 8, stimulation field 180A corresponds to the initial electrode configuration of electrode A, stimulation field 180B corresponds to the alternative electrode configuration of electrodes A and B, stimulation field 180C corresponds to the alternative electrode configuration of electrodes A, B, and C, and stimulation field 180D corresponds to the alternative electrode configuration of electrodes A, B, C, and D.

Field width scale 178 includes multiple dotted lines that indicate the distance the stimulation field reaches out from lead 176. Field width scale 178 is provided with each of stimulation fields 180 in order to review the relative sizes of each stimulation field. For example, field width scale 178 shows that stimulation field 180A provides a wider stimulation field than stimulation field 180D. Each dotted line of field width scale 178 may correspond to a respective distance from lead 176 in a scale of millimeters, centimeters, inches, or any other distance scale.

Side views 174 include side views of each of stimulation fields 180A, 180B, 180C, and 180D with respect to the side view of lead 176. As shown in side views 174, as more electrodes are used to generate the stimulation fields 180A-180D, the length of the stimulation field increases in size. In other words, stimulation field 180A from one electrode provides a shorter stimulation field along the length of lead 174 than stimulation field 180D provided by 13 electrodes. Although not shown in FIG. 9, a field height scale (such as field width scale 178) may also be shown in conjunction with the side views of stimulation fields in side views 174.

Axial views 172 and side views 174 may be referred to as 2D representations of the stimulation fields. In some examples, programmer 20 may allow a user to rotate each stimulation field 180 as desired. In other examples, one or more 3D representation of each stimulation field may be displayed. Programmer 20 may receive user input that rotates, spins, or moves the stimulation field in three dimensions in order to view the stimulation field. In some examples, stimulation fields 180, and possibly lead 176, may be shown in conjunction with a representation of patient anatomy. Programmer 20 may thus display stimulation fields 180 over anatomical structures so that the user can view whether or not stimulation fields 180 stimulate desired anatomical regions and/or undesirable anatomical regions.

In some examples, programmer 20 may generate and display stimulation fields 180 as different colors. The different colors may be used to key each stimulation field to a respective electrode combination. In other examples, different colors or patterns of stimulation fields 180 may indicate a comparison to the initial electrode combination. For example, different colors of stimulation fields 180 may be indicative of the power consumption value. Green color shades may indicate less power consumption and red color shades may indicate more power consumption, for example. In other examples, a color or pattern of stimulation fields 180 may indicate how similar the stimulation field is to the initial electrode combination. In this manner, representation 170 may provide more information about the alternative electrode combinations than merely a graphic representation of the stimulation fields.

Figure 10:
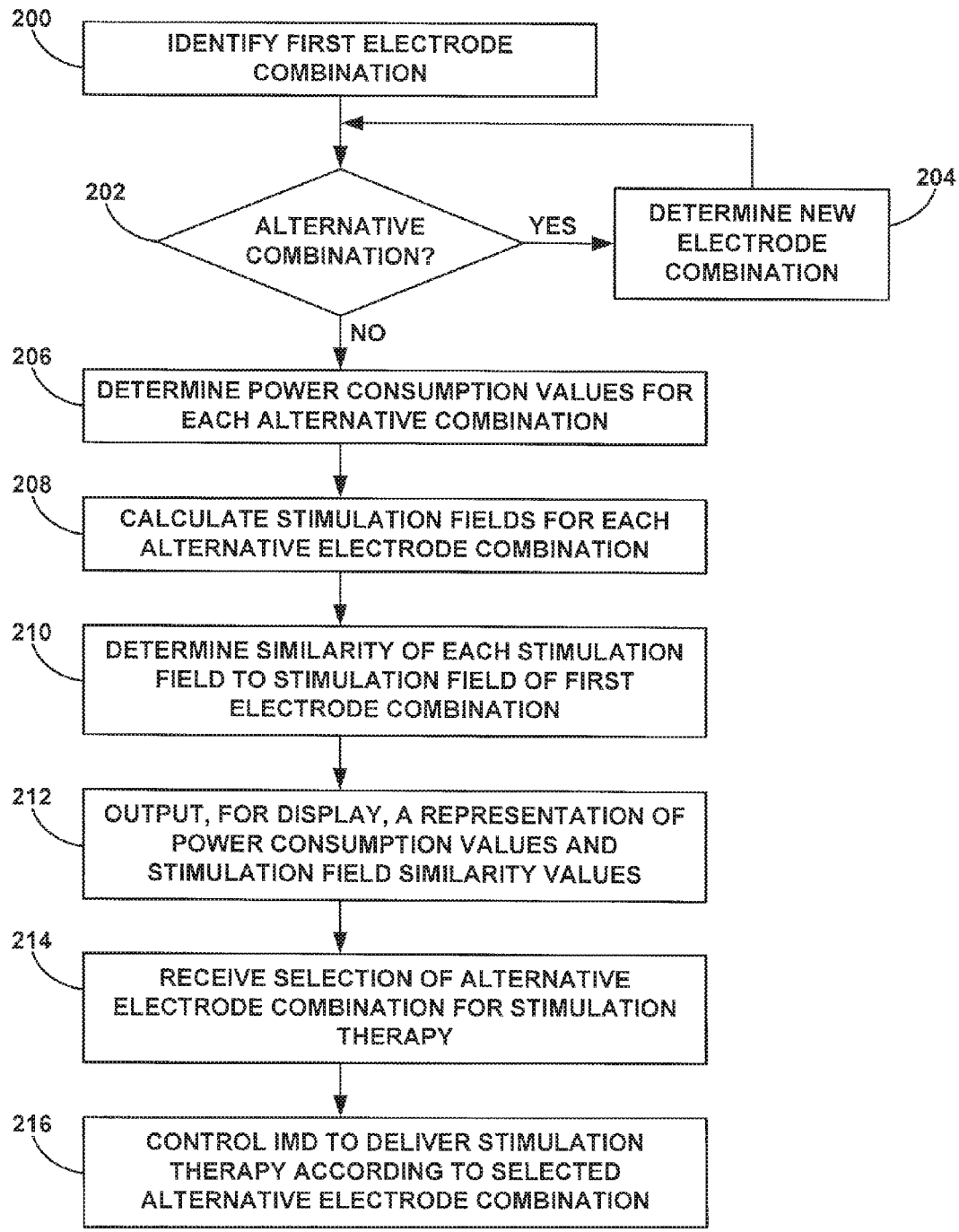
FIG. 10 is a flow diagram of an example process for determining alternative electrode combinations according to the present disclosure.

FIG. 10 is a flow diagram of an example process for determining alternative electrode combinations according to the present disclosure. The process of FIG. 10 will be described with regard to processor 130 of programmer 20. However, this process, or portions of the process, may be performed by other devices such as controller 14, IMD 100, networked server 146, or computing devices 150. In this manner, one device, or several networked devices, may perform the process of FIG. 10.

As shown in FIG. 10, processor 130 identifies a first electrode combination (e.g., set of one or more electrodes or an initial electrode combination) (200). Processor 130 may identify the first electrode combination by receiving user input that defines the first electrode combination or from another therapy programmer. In other examples processor 130 may identify the first electrode combination from a selected stimulation program, one or more electrodes determined as available for stimulation from a user, or as corresponding to a user or system desired anatomical region or direction with respect to the lead. If processor 130 determines that there is an alternative electrode combination available ("YES" branch of block 202), processor 130 may determine the new alternative electrode combination (204). Processor 130 may determine the new alternative electrode combination by adding additional electrodes to the electrodes of the initial electrode combination or the previously generated alterative electrode combination.

If processor 130 determines that there are no more alterative electrode combinations available ("NO" branch of block 202), processor 130 may then determine (e.g., calculate or measure) power consumption values for each of the alterative electrode combinations (206). Processor 130 also calculates stimulation fields for each of the alterative electrode combinations (208). Using the calculated stimulation fields, processor 130 also determines the similarity of the stimulation field of each alternative electrode combination to the stimulation field of the first electrode combination (210). For example, processor 130 may calculate a field similarity score such as a Sorensen-Dice coefficient.

Once processor 130 has determined attributes for each of the alterative electrode combinations, processor 130 may output, for display, a representation of the power consumption values and stimulation field similarity values for one or more of the alterative electrode combinations (212). For example, processor 130 may control user interface 136 to display the information of Table 1 and/or the stimulation fields of representation 170 of FIG. 9. Via user interface 136, processor 130 receives user selection of one of the alterative electrode combination for stimulation therapy (214). Processor 130 then controls an IMD (e.g., controller 14 or IMD 100) to deliver stimulation therapy according to the selected alternative electrode combination (216). In other examples, as described herein, processor 130 may automatically select one of the alterative electrode combinations. Processor 130 may request user confirmation of the selected alterative electrode combination and/or present information about the selected alterative electrode combination.

Processor 130 may initiate the process of FIG. 10 in a variety of situations. Processor 130 may propose alterative electrode combinations any time that processor 130 receives a user defined electrode combination intended for stimulation therapy. In other examples, processor 130 may propose alterative electrode combinations when a therapy program is first selected to be used for stimulation therapy. Alternatively, processor 130 may propose alterative electrode combination in response to detecting inadequate battery life or some other unexpected or undesirable power usage of the IMD. Processor 130 may thus propose alterative electrode combinations in order to extend battery life of the system or otherwise improve the amount of time for which the IMD can deliver stimulation therapy between recharging intervals.

The process of FIG. 10 is directed to determining alternative electrode combinations using the same or similar stimulation parameters such as pulse width, current or voltage amplitude, pulse frequency, etc. However, processor 130 may perform an alternative process for FIG. 10 in which different sets of stimulation parameters, not just different electrode combinations, are determined. These different sets of stimulation parameters may include alternatives to one or more of the pulse frequency, pulse width, duty cycle, current or voltage amplitude, or any other stimulation parameter. For each of these alternative sets of stimulation parameters determined by processor 130, processor 130 may determine respective power consumption values and stimulation field similarity values. Processor 130 may then use an alternative set of stimulation parameters to control delivery of stimulation therapy to the patient. A process of selecting different sets of stimulation parameters may require one or more constraints that limit the system to certain ranges of values such as minimum or maximums for number of electrodes, current or voltage amplitude, pulse width, pulse frequency, etc.

Figure 11:
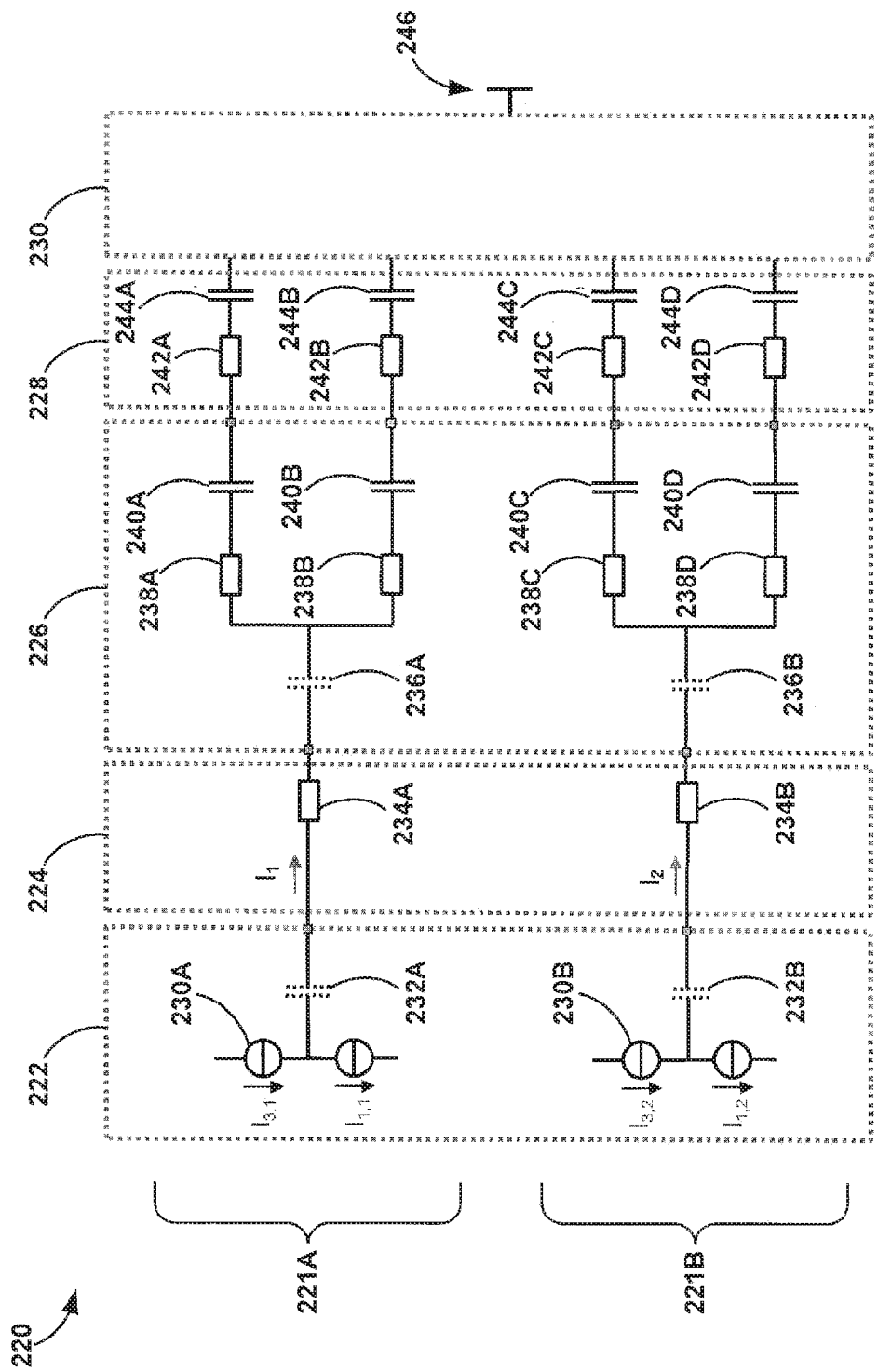
FIG. 11 is a conceptual diagram illustrating an example monopolar stimulation circuit that represents a system impedance.

FIG. 11 is a conceptual diagram illustrating an example monopolar stimulation circuit that represents elements of the system that may contribute to the impedance of one or more electrodes for each of a respective current source. Circuit 220 may be representative of a stimulation circuit associated with system 10, for example. Circuit 220 may represent various sources of current, capacitance, and resistance that contributes to the overall impedance of the system for any given electrode or electrode combination. As shown in FIG. 11, circuit 220 includes stimulator block 222 representing elements of controller 14 or IMD 100 (which may include two push-pull current sources 230A and 230B as shown, one push-pull current source, or three or more push-pull current sources), lead cable block 224 representing elements of connecting cable 16, second module block 226 representing elements of second module 17, lead block 228 representing elements of lead 22 and electrodes thereof, and tissue block 230 representing the resistance of tissue between the electrodes and ground terminal 246. These components of circuit 220 may represent or model one or more electrical components that may contribute to the overall system impedance and power dissipation of the circuit. Although circuit 220 may represent actual electrical components present in the system in some examples, circuit 220 may be a general approximation of the electrical characteristics of one or more electrical components of a stimulation circuit for modeling purposes.

When measuring, calculating, or otherwise determining the impedance or resistance of the circuit for an electrode combination, various components of the entire system, including the tissue through which the electrical signal propagates, may be considered. Sub-circuit 221A may include those components used to provide stimulation from current source 230A and sub-circuit 221B includes those components used to provide stimulation from push-pull current source 230B. In the example of sub-circuit 221A, contributors to the overall impedance (or also referred to as a collective impedance for an electrode combination) or overall load of push-pull current source 230A may include blocking capacitor 232A of stimulator block 222 and resistance 234A of one or more conductors of lead block 228. Additional contributors to the load impedance of push-pull current source 230A of sub-circuit 221A may include components of second module block 226 such as one or more blocking capacitors 236A, resistors 238A and 238B of a switch matrix, blocking capacitors 240A and 240B, components of lead block 228 such as lead resistors 242A and 242B (e.g., conductive traces or conductors) and corresponding capacitors 244A and 244B representing the respective electrodes (e.g., the interface between electrodes and adjacent tissue), and impedance of tissue block 230 before the electrical current reaches ground terminal 246 (e.g., the housing of controller 14 or a return electrode). In some examples, tissue block 230 may represent the R-matrix, or resistance matrix, or Z-matrix, or impedance matrix, of the electrodes of the lead. The R-matrix and Z-matrix may be described as the brain tissue spreading resistance or impedance, respectively, in some examples and be used as a representation of the tissue resistance or impedance that corresponds to each electrode. In some examples, the R-matrix or Z-matrix may be measured via test pulses or other excitation waveforms (e.g., square wave currents, voltages, etc.) generated from the stimulation generator (e.g., one or more current sources) or separate measurement module (e.g., a measurement module 111 of FIG. 5 that includes both an excitation source and measurement circuitry to measure the response to the excitation pulse(s) that allows measurement of the R-matrix or Z-matrix). Sub-circuit 221A is representative of two electrodes being driven, but any number of electrodes may be represented by respective components such as resistance 238A, capacitor 240A, resistor 242A, and capacitor 244A.

Impedances for sub-circuit 221B may be similar to the components of sub-circuit 221A. For example, sub-circuit 221B may include push-pull current source 230B, blocking capacitor 232B, resistor 234B, blocking capacitor 236B, resistors 238C and 238D, capacitors 240C and 240D, resistors 242C and 242D, and capacitors 244C and 244D. Each of the components of sub-circuits 221A and 221B represent one or more of those components, so the illustration of only one component is to simplify the discussion of possible elements that contribute to the system and/or load impedance. In other examples, additional or fewer sources of capacitance and/or resistance may be present in the system. For example, blocking capacitors 236A and 240A and resistor 238A, 238B, 242A and 242B may not be present in IMD 100 that includes the simulation generator 108 (e.g., one or more current sources) and switch module 110. Circuit 220 represents a monopolar stimulation configuration. However, similar circuits can be used to model or represent components that contribute to impedances for bipolar stimulation configurations. Other models can be used to represent components that contribute to impedances for multi-implant set-ups.

Power consumption values calculated or measured for each respective sub-circuit 221A and 221B may incorporate the effects of current injected to tissue block 230 by the other sub-circuit in multiple current source examples. For example, current (e.g., $I_{PG1}$) from push-pull current source 230A applied to tissue block 230, which has a resistance, which can be represented by the R-matrix or Z-matrix, creates a voltage potential on the electrodes and components of sub-circuit 221B because the same tissue is in electrical contact with all electrodes of both sub-circuits 221A and 221B. In this manner, presence of a current from sub-circuit 221A causes a change of the voltage potential at push-pull current source 230B of sub-circuit 221B which may require a change in the supply rail voltages HV+,2 and/or HV−,2 of push-pull current source 230B in order to keep driving the electrode combination of sub-circuit 221B with the desired current. This change in supply rail voltage(s) may also increase the power drawn by push-pull current source 230B from these rails. This phenomenon may be represented by using the R-matrix or Z-matrix described herein and is further discussed with respect to FIG. 12.

Figure 12:
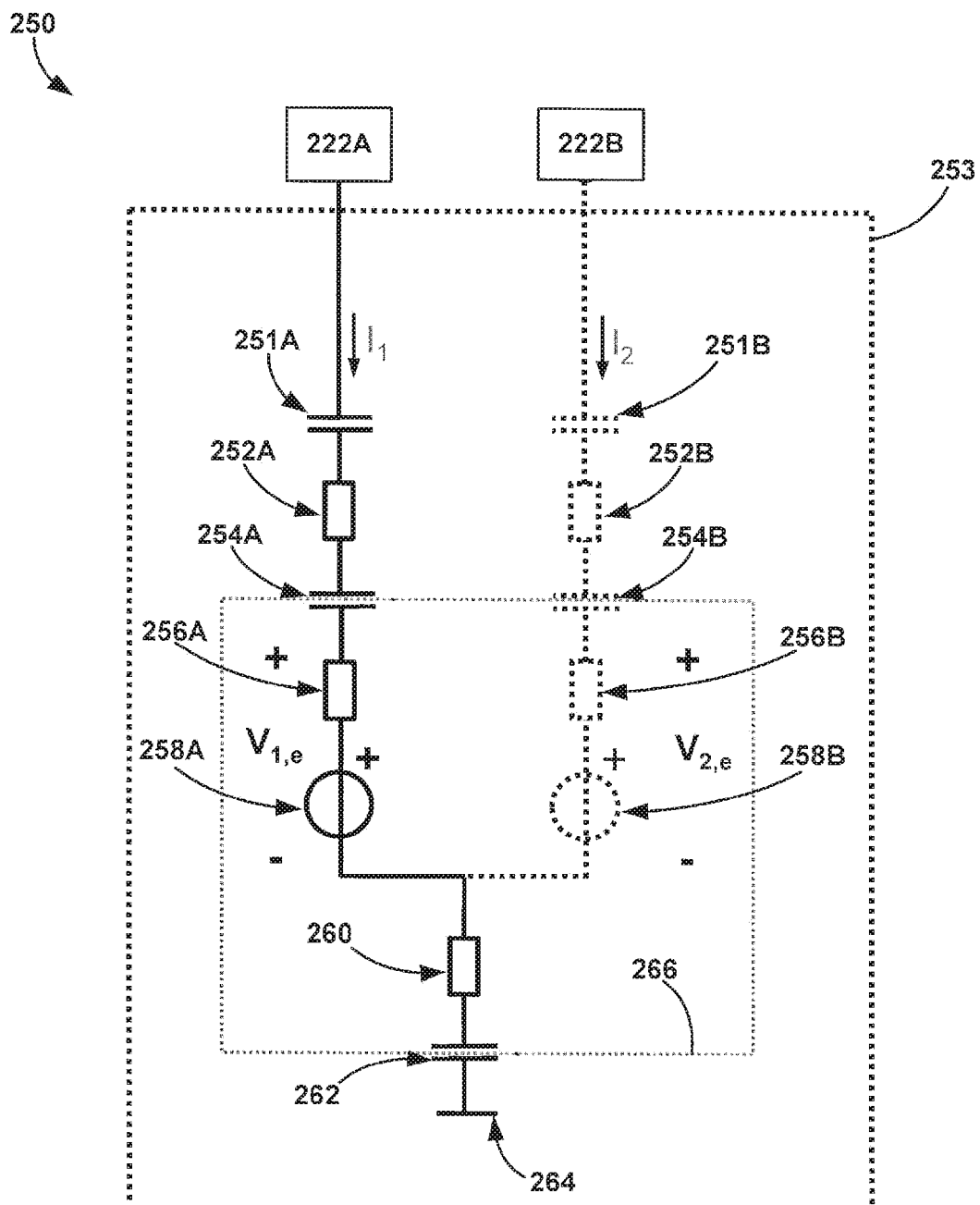
FIG. 12 is a conceptual diagram illustrating an example load model for multiple stimulation generators in a system.

FIG. 12 is a conceptual diagram illustrating an example load model for multiple stimulation generators in a system. Load model 250 may represent circuits similar to sub-circuits 221A and 221B of FIG. 11 and illustrate the coupling that can occur between electrodes of the different sub-circuits each having its own current source. Load model 250 includes stimulator blocks 222A and 222B which include the respective current sources and blocking capacitors for sub-circuits 221A and 221B of FIG. 11. Each stimulator block 222A and 222B can inject a current, $I_1$ and $I_2$, respectively, into the stimulation load 253 represented by the large dotted-line box. Capacitors 251A and 251B represent capacitances in the respective circuit due to blocking capacitors, for example, and resistors 252A and 252B represent resistances in the respective circuit due to switches, conductors, etc. Capacitors 254A and 254B represent the capacitances of the electrode-tissue interface of the electrode combinations for each circuit.

Characteristics of tissue 266 are represented by the small dotted-line box. Tissue 266 may be a more detailed model of tissue block 230 in FIG. 11. The elements within tissue 266 represent the elements of the R-matrix or Z-matrix as discussed herein. For example, resistor 256A represents the resistance of tissue associated with the electrode combination driven by current from stimulation block 222A and resistor 256B represents the resistance of tissue associated with the electrode combination driven by current from stimulation block 222B. Resistor 260 may represent the bulk resistance of the tissue far from the electrodes (which may be relatively small), and capacitor 262 may represent the capacitance of the controller housing when used as the grounded (264) return electrode in this example monopolar stimulation load model. If each of stimulation block 222A and 222B, and their respective circuit elements, operated independently or into electrically isolated tissue, the load for each respective current source would not affect the load to the other current source.

However, this is not the case when multiple current sources are providing current to the same electrically coupled tissue 266. Current provided by one current source instead creates a voltage potential across the components of the other circuit because all electrodes are electrically coupled by the same conductive tissue in which they reside (e.g., brain tissue). Controlled voltage source 258A represents the change in voltage stimulation block 222A experiences due to the current injected by stimulation block 222B, while controlled voltage source 258B represent the change in voltage stimulation block 222B experiences due to the current injected by stimulation block 222A. The voltage of each controlled source 256A and 256B may be calculated by the product of the transresistance ($R_x$) for the electrode combinations connected to stimulation block 222A and 222B and the current ($I_1$ or $I_2$) injected into the tissue by the other circuit. $V_{1,e}$ and $V_{2,e}$ represents the voltages developed across the spreading resistance for each electrode combination for each circuit (which may be the main contributor to tissue resistance). In this manner, the known or measured R-matrix or Z-matrix can be used to establish this relationship and determine the arising voltages and currents for the tissue 266. A simple representation of the resistance matrix is provided below in equation 2:

$$\begin{pmatrix} V_{1,e} \\ V_{2,e} \end{pmatrix} = \begin{pmatrix} R_{11} & R_x \\ R_x & R_{22} \end{pmatrix} \begin{pmatrix} I_1 \\ I_2 \end{pmatrix}, \quad (2)$$

where $V_{1,e}$ and $V_{2,e}$ are the voltages developed across the spreading resistance of each electrode combination of each sub-circuit, R11 is the resistance of resistor 256A, R22 is the resistance of resistor 256B, and $R_x$ is the transresistance of the tissue. A larger matrix may be used to represent each electrode, or electrode combination, in some examples, while a larger matrix may be used to represent more than two stimulation blocks. If a full matrix is derived for all electrodes of a lead (e.g., a 40×40 matrix for 40 electrodes of a lead), then the system may derive all other resistance or impedance matrices for any other smaller matrices such as the example 2×2 R-matrix described above. The R-matrix above may be determined by measuring the response to test stimulation pulses applied to the tissue for the selected electrode combinations and then used to calculate or otherwise determine the power consumption values for these selected electrode combinations that may or may not be affected by current delivered via another electrode combination and corresponding current source. Although the R-matrix is shown, the Z-matrix, or impedance matrix, may also be calculated be incorporating reactances of the tissue, for example, capacitive coupling between sets of electrode combinations. Programmer 20, or any other device herein, may use the R-matrix or Z-matrix described herein to calculate or determine power consumption values for certain stimulation parameters, including electrode combinations, when multiple current sources may be present in the overall system.

While techniques described herein are discussed primarily in regards to DBS therapy, one or more such techniques may be applied to treat disorders such as chronic pain disorders, urinary or fecal incontinence, sexual dysfunction, obesity, gastroparesis, and may involve other types of stimulation such as spinal cord stimulation, cardiac stimulation, pelvic floor stimulation, sacral nerve stimulation, peripheral nerve stimulation, peripheral nerve field stimulation, gastric stimulation, or any other electrical stimulation therapy.

In addition, it should be noted that system 10 may not be limited to treatment or monitoring of a human patient. In alternative examples, system 10 may be implemented in non-human patients, e.g., primates, canines, equines, pigs, and felines. These other animals may undergo clinical or research therapies that my benefit from the subject matter of this disclosure.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules and devices (e.g., controller 14, second module 17, IMD 100, or programmer 20) and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A method comprising:
    identifying, by one or more processors, a set of one or more electrodes configured to deliver electrical stimulation therapy via a lead, the lead comprising a plurality of electrodes arranged in a complex electrode array geometry, wherein the plurality of electrodes comprises the set of one or more electrodes;
    determining, by the one or more processors and based on the set of one or more electrodes, one or more alternative electrode combinations for delivering electrical stimulation therapy, wherein each of the one or more alternative electrode combinations are associated with a respective power consumption value lower than a power consumption value associated with the set of one or more electrodes;
    calculating, by the one or more processors and for each of the one or more alternative electrode combinations, a respective field similarity score with respect to the set of one or more electrodes; and
    outputting, by the one or more processors, a representation of at least one of the one or more alternative electrode combinations for selection in at least partially defining electrical stimulation therapy, the representation comprising an indication of at least one of the respective power consumption values or the respective field similarity scores.

2. The method of claim 1, wherein each of the one or more alternative electrode combinations comprises a greater number of electrodes than the set of one or more electrodes.

3. The method of claim 1, wherein each alternative electrode combination comprises the set of one or more electrodes.

4. The method of claim 1, wherein determining the one or more alternative electrode combinations comprises iteratively determining each of the one or more alternative electrode combinations such that successive alternative electrode combinations add one or more electrodes to all electrodes defined by prior alternative electrode combinations.

5. The method of claim 4, wherein successive alternative electrode combinations include electrodes at increasing distances from one or more electrodes of the set of one or more electrodes.

6. The method of claim 1, wherein:
a first alternative electrode combination of the one or more alternative electrode combinations comprises a first number of electrodes less than or equal to a second number of electrodes of the set of one or more electrodes; and
a first power consumption value associated with the first alternative electrode combination is less than the power consumption value associated with the second number of electrodes of the set of one or more electrodes.

7. The method of claim 1, further comprising calculating the respective power consumption values for the set of one or more electrodes and the one or more alternative electrode combinations by calculating, for the set of one or more electrodes and the one or more alternative electrode combinations, the power dissipation from at least one of an R-matrix, a Z-matrix, or an electrical model of a system delivering electrical stimulation using one of a common set of stimulation parameter or different sets of stimulation parameters.

8. The method of claim 1, further comprising ranking the alternative electrode combinations based on the respective power consumption value, and wherein the representation of at least some of the one or more alternative electrode combinations is indicative of the ranking.

9. The method of claim 1, wherein calculating the respective field similarity scores comprises:
determining an original stimulation field deliverable by the set of one or more electrodes;
determining, for each of the alternative electrode combinations, a respective stimulation field deliverable by the respective alternative electrode combination;
comparing, for each of the alternative electrode combinations, the respective stimulation field deliverable by the respective alternative electrode combination to the original stimulation field deliverable by the set of one or more electrodes; and
outputting, for each of the alternative electrode combinations, an indication of the comparison.

10. The method of claim 9, wherein the comparison for each of the alternative electrode combinations is based on a Sorensen-dice coefficient between the original stimulation field and the respective stimulation fields deliverable by the respective alternative electrode combinations.

11. The method of claim 1, further comprising outputting, for each of the set of one or more electrodes and at least one of the one or more alternative electrode combinations, a visual representation of a stimulation field deliverable via the respective electrode combination.

12. The method of claim 1, further comprising:
receiving a selection of one of the alternative electrode combinations; and
controlling delivery of electrical stimulation therapy to a patient according to the selected alternative electrode combination.

13. The method of claim 1, wherein the electrical stimulation therapy comprises deep brain stimulation therapy.

14. A system comprising:
one or more processors configured to:
identify a set of one or more electrodes configured to deliver electrical stimulation therapy via a lead, the lead comprising a plurality of electrodes arranged in a complex electrode array geometry, wherein the plurality of electrodes comprises the set of one or more electrodes;
determine, based on the set of one or more electrodes, one or more alternative electrode combinations for delivering electrical stimulation therapy, wherein each of the one or more alternative electrode combinations are associated with a respective power consumption value lower than a power consumption value associated with the set of one or more electrodes;
calculate, for each of the one or more alternative electrode combinations, a respective field similarity score with respect to the set of one or more electrodes; and
output a representation of at least one of the one or more alternative electrode combinations for selection in at least partially defining electrical stimulation therapy, the representation comprising an indication of at least one of the respective power consumption values or the respective field similarity scores.

15. The system of claim 14, wherein each of the one or more alternative electrode combinations comprises a greater number of electrodes than the set of one or more electrodes.

16. The system of claim 14, wherein each alternative electrode combination comprises the set of one or more electrodes.

17. The system of claim 14, wherein the one or more processors are configured to determine the one or more alternative electrode combinations by iteratively determining each of the one or more alternative electrode combinations such that successive alternative electrode combinations add one or more electrodes to all electrodes defined by prior alternative electrode combinations.

18. The system of claim 14, wherein:
a first alternative electrode combination of the one or more alternative electrode combinations comprises a first number of electrodes less than or equal to a second number of electrodes of the set of one or more electrodes; and
a first power consumption value associated with the first alternative electrode combination is less than the power consumption value associated with the second number of electrodes of the set of the set of one or more electrodes.

19. The system of claim 14, wherein the one or more processors are configured to calculate the respective power consumption values for each of the set of one or more electrodes and the one or more alternative electrode combinations by calculating, for the set of one or more electrodes and the one or more alternative electrode combinations, the power dissipation from at least one of an R-matrix, a Z-matrix, or an electrical model of a system delivering electrical stimulation using one of a common set of stimulation parameter or different sets of stimulation parameters.

20. The system of claim 14, wherein the one or more processors are configured to calculate the respective field similarity scores by:
- determining an original stimulation field deliverable by the set of one or more electrodes;
- determining, for each of the alternative electrode combinations, a respective stimulation field deliverable by the respective alternative electrode combination;
- comparing, for each of the alternative electrode combinations, the respective stimulation field deliverable by the respective alternative electrode combination to the original stimulation field deliverable by the set of one or more electrodes; and
- outputting, for each of the alternative electrode combinations, an indication of the comparison.

21. The system of claim 14, wherein the one or more processors are configured to output, for each of the set of one or more electrodes and at least one of the one or more alternative electrode combinations, a visual representation of a stimulation field deliverable via the respective electrode combination.

22. The system of claim 14, further comprising:
- an external programmer that comprises the one or more processors and a user interface, wherein the external programmer is configured to:
  - receive, via the user interface, a selection of one of the alternative electrode combinations; and
  - control, by the one or more processors, delivery of electrical stimulation therapy to a patient according to the selected alternative electrode combination; and
- an implantable medical device configured to receive the selected alternative electrode combination and deliver the electrical stimulation therapy according to the selected alternative electrode combination.

23. The system of claim 14, wherein the electrical stimulation therapy comprises deep brain stimulation therapy.

24. A non-transitory computer-readable medium comprising instructions that, when executed, cause one or more processors to:
- identify a set of one or more electrodes configured to deliver electrical stimulation therapy via a lead, the lead comprising a plurality of electrodes arranged in a complex electrode array geometry, wherein the plurality of electrodes comprises the set of one or more electrodes;
- determine, based on the set of one or more electrodes, one or more alternative electrode combinations for delivering electrical stimulation therapy, wherein each of the one or more alternative electrode combinations are associated with a respective power consumption value lower than a power consumption value associated with the set of one or more electrodes;
- calculate, for each of the one or more alternative electrode combinations, a respective field similarity score with respect to the set of one or more electrodes; and
- output a representation of at least one of the one or more alternative electrode combinations for selection in at least partially defining electrical stimulation therapy, the representation comprising an indication of at least one of the respective power consumption values or the respective field similarity scores.

* * * * *